US009125935B1

(12) United States Patent
Walter et al.

(10) Patent No.: US 9,125,935 B1
(45) Date of Patent: Sep. 8, 2015

(54) PROBIOTICS AND METHODS OF OBTAINING SAME

(75) Inventors: Jens Walter, Lincoln, NE (US); Bob Hutkins, Lincoln, NE (US); Thomas Burkey, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 13/484,372

(22) Filed: May 31, 2012

Related U.S. Application Data

(60) Provisional application No. 61/491,406, filed on May 31, 2011.

(51) Int. Cl.
| A61K 35/74 | (2015.01) |
| A23L 1/29 | (2006.01) |
| A61P 1/14 | (2006.01) |
| A61K 35/744 | (2015.01) |
| A61K 35/745 | (2015.01) |
| A23L 1/30 | (2006.01) |

(52) U.S. Cl.
CPC . *A61K 35/74* (2013.01); *A23L 1/29* (2013.01); *A23L 1/3014* (2013.01); *A61K 35/744* (2013.01); *A61K 35/745* (2013.01)

(58) Field of Classification Search
None
See application file for complete search history.

(56) References Cited

U.S. PATENT DOCUMENTS

| 6,706,287 | B2 | 3/2004 | Ranganathan et al. |
| 6,841,149 | B1 | 1/2005 | Spangler et al. |
| 7,101,565 | B2 | 9/2006 | Monte |
| 8,137,706 | B2 | 3/2012 | Al-Ghazzewi et al. |
| 2003/0147857 | A1 | 8/2003 | Monte |
| 2004/0086491 | A2 | 5/2004 | Monte |
| 2006/0093592 | A1 | 5/2006 | Cheruvanky et al. |
| 2009/0041736 | A1 | 2/2009 | Sprenger et al. |
| 2011/0177044 | A1 | 7/2011 | Thomas et al. |
| 2012/0009256 | A1 | 1/2012 | Porubcan et al. |
| 2012/0052152 | A1 | 3/2012 | Armentrout |

OTHER PUBLICATIONS

Thammarutwasik, P. et al. 2009. Prebiotics—A Review. Songklanakarin Journal of Science and Technology 31(4):401-408. specif. p. 402, col. 2, para. 1.*
Dickinson, E. 2003. Hydrocolloids at interfaces and the influence on the properties of dispersed systems. Food Hydrocolloids 17:25-39. specif. p. 25.*
Alles et al., "Effect of transgalactooligosaccharides on the composition of the human intestinal microflora and on putative risk markers for colon cancer1 '2'3," *Am. J. Clin. Nutr.*, 1999, 69:980-91.
Bengmark et al., "Prebiotics and Synbiotics in Clinical Medicine," *Nutr. Clin. Pract.*, 2005, 20:244-61.
Bengmark, "Bioecologic Control of Acute and Chronic Diseases: The Role of Pro-, Pre- and Synbiotics," *Kuwait Med. J*, 2007, 39(3):216-226.

Bouhnik et al., "The capacity of nondigestible carbohydrates to stimulate fecal bifidobacteria in heathly humans: a double-blind, randomized, placebo-controlled, parallel-group, dose-response relation study[1-3]," *Am. J. Clin. Nutr.*, 2004, 80:1658-64.
Cole et al., "The Ribosomal Database Project: improved alignments and new tools for rRNA analysis," *Nuc. Acids Res.*, 2009, 37:D141-5.
de Vrese et al., "Probiotics, Prebiotics, and Synbiotics," *Adv. Biochem. Eng. Biotechnol.*, 2008, 111:1-66.
Fooks et al., "Probiotics as modulators of the gut flora," *Br. J. Nutr.*, 2002, 88 (Supplem 1):S39-49.
Geier et al., "Inflammatory bowel disease: Current insights into pathogenesis and new therapeutic options; probiotics, prebiotics, and synbiotics," *Int. J. Food Microbiol.*, 2007, 115:1-11.
Gupta et al., "Probiotics," *Indian J. Med. Microbiol.*, 2009, 27:202-9.
Haskey and Dahl, "Synbiotic Therapy: A Promising new Adjunctive Therapy for Ulcerative Colitis," *Nutr. Rev.*, 2006, 64:132-8.
Jackson et al., "Bacterial genotyping by 16S rRNA mass cataloging," *BMC Bioinformatics*, 2006, 7:321.
Martínez et al., "Diet-Induced Metabolic Improvements in a Hamster Model of Hypercholesterolemia Are Strongly Linked to Alterations of the Gut Microbiota," *Appl. Environ. Microbiol.*, 2009, 75:4175-84
Martinez et al., "Resistant Starches Types 2 and 4 Have Differential Effects on the Composition of the Fecal Microbiota in Human Subjects," *PLos One*, 2010, 5:e15046.
Ovreas et al., "Distribution of bacterioplankton in meromictic Lake Saelenvannet, as determined by denaturing gradient gel electrophoresis of PCR-amplified gene fragments coding for16S rRNA," *Appl. Environ. Microbio.*, 1997, 63:3367-73.
Rastall et al., "Modulation of the microbial ecology of the human colon by probiotics, prebiotics, and synbiotics to enhance human health: An overview of enabling science and potential applications," *FEMS Microbiol. Ecol.*, 2005, 52:145-52.
Rastall, "Bacteria in the Gut: Friends and Foes and How to Alter the Balance," *J. Nutr.*, 2004, 134:2022S-2026S.
Rinttila et al., "Development of an extensive set of 16S rDNA-targeted primers for quantification of pathogenic and indigenous bacteria in fecal samples by real-time PCR," *J. Appl. Microbiol.*, 2004, 97:1166-77.
Roberfroid, "Prebiotics and synbiotics: concepts and nutritional properties," *Br. J. Nutr.*, 1998, 80:S197-202.
Seksik et al., "Is there any place for alimentary probiotics, prebiotics or synbiotics, for patients with inflammatory bowel disease?" *Mol. Nutr. Food Res.*, 2008, 52:906-12.
Shadid et al., "Effects of galactooligosaccharide and long-chain fructooligosaccharide supplementation during pregnancy on maternal and neonatal microbiota and immunity—A randomized, double-blind, placebo-controlled study[1-3]," *Am. J. Clin. Nutr.*, 2007, 86:1426-37.
Steed et al., "Prebiotics, synbiotics and inflammatory bowel disease," *Mol. Nutr. Food Res.*, 2008, 52:898-905.

(Continued)

*Primary Examiner* — John S Brusca
*Assistant Examiner* — Sharon M Papciak
(74) *Attorney, Agent, or Firm* — Fish & Richardson P.C.

(57) ABSTRACT

This disclosure describes novel probiotics, and also describes novel methods by which such probiotics can be obtained.

7 Claims, 14 Drawing Sheets

(56) References Cited

OTHER PUBLICATIONS

Subramanian et al., "Bacteria in the pathogenesis of inflammatory bowel disease," *Curr. Opin. Infect. Dis.*, 2006, 19:475-84.

Tannock et al., "Analysis of the Fecal Microflora of Human Subjects Consuming a Probiotic Product Containing *Lactobacillus rhamnosus*DR20," *Appl. Environ. Microbio.*, 2000, 66:2578-88.

Tannock et al., "Impact of Consumption of Oligosaccharide-Containing Biscuits on the Fecal Microbiota of Humans," *Appl. Environ. Microbio.*, 2004, 70:2129-36.

Tuohy et al., "Modulation of the human gut microflora towards improved health using prebiotics—assessment of efficacy," *Curr. Pharm. Des.*, 2005, 11:75-90.

Turnbaugh et al., "A core gut microbiome in obese and lean twins," *Nature*, 2009, 457:480-4.

Urakawa et al., "16S rDNA genotyping using PCR/RFLP (restriction fragment length polymorphism) analysis among the family Vibrionaceae," *FEMS Microbiol. Lett.*, 1997, 152:125-32.

Walter et al., "Detection and Identification of Gastrointestinal *Lactobacillus* Species by Using Denaturing Gradient Gel Electrophoresis and Species-Specific PCR Primers," *Appl. Environ. Microbio.*, 2000, 66:297-303.

Walter et al., "Detection of *Lactobacillus, Pediococcus, Leuconostoc,* and *Weissella* Species in Human Feces by Using Group-Specific PCR Primers and Denaturing Gradient Gel Electrophoresis," *Appl. Environ. Microbio.*, 2001, 67:2578-85.

Weisburg et al., "16S Ribosomal DNA Amplification for Phylogenetic Study," *J. Bacteriol.*, 1991, 173:697-703.

Davis et al., "A dose dependant impact of prebiotic galactooligosaccharides on the intestinal microbiota of healthy adults," Int'l J Food Microbiol., 2010, 144:285-292. specif. pp. 286-289.

Vulevic et al. "Modulation of the fecal microflora profile and immune function by a novel trans-galactooligosaccharide mixture (B-GOS) in healthy elderly volunteers," Am J Clin. Nutrition, 2008, 88:1438-1446. specif. pp. 1439, 1441.

Kohmoto et al., "Dose-response test of isomaltooligosaccharides for increasing fecal bifidobacterial," Agric.Biol. Che. 55(8), 2157-2159, 1991.

\* cited by examiner

A

Dosage of GOS

B

Dosage of GOS

PROBIOTICS AND METHODS OF OBTAINING SAME

CROSS REFERENCE TO RELATED APPLICATIONS

This application claims benefit under 35 U.S.C. 119(e) to U.S. Application No. 61/491,406 filed May 31, 2011.

TECHNICAL FIELD

This disclosure generally relates to microbiology and, more specifically, to probiotics.

BACKGROUND

The large intestine of humans harbors a complex, cell rich, and diverse microbial community consisting of hundreds of different bacterial species. Included within this microbiota are organisms whose presence is associated with, or that contribute to the health of the host, referred to as probiotics. Probiotics are defined as microbial cell preparations or components of microbial cells that have a beneficial effect on the health and well-being of the host. Probiotics have been identified from a number of different genera including, but not limited to, *Lactobacilli, Streptococcus* and *Bifidobacterium*, which have many species that are indigenous to the human digestive tract.

Probiotics are thought to exert their beneficial effects by displacing pathogenic enteric bacteria from the intestinal mucosa due, at least, in part, to competitive binding. For example, enteric pathogens such as enteropathogenic *Escherichia coli* (EPEC), enterotoxigenic *E. coli* (ETEC), *Salmonella enteriditis, Yersina pseudotuberculosis* and *Listeria monocytogenes* must be able to successively colonize an animal's gastrointestinal tract in order to cause disease.

SUMMARY

This disclosure describes novel probiotics, and also describes novel methods by which such probiotics can be obtained.

In one aspect, a substantially pure population of bacteria is provided, wherein the bacteria is *Bifidobacterium adolescentis* strain BD1. In some embodiments, the substantially pure population of bacteria further includes galactooligosaccharide (GOS).

In another aspect, a composition comprising *Bifidobacterium adolescentis* strain BD1 and GOS is provided. In some embodiments, the composition further includes a pharmaceutically acceptable carrier. Representative pharmaceutically acceptable carrier include, without limitation, a liquid carrier, a gel-based carrier, an oleaginous carrier, and an emulsion. Typically, such a composition can be in the form of a powder, a granule, a tablet, a capsule, a liquid suspension, a paste, and a syrup.

In still another aspect, a foodstuff is provided that includes (a) an effective amount of the substantially pure population of bacteria or of the composition and (b) at least one food or feed ingredient. In certain embodiments, the at least one food ingredient is a dairy product (e.g., yogurt).

In yet another aspect, a method for establishing or maintaining a healthy gastrointestinal flora in an animal is provided. Such a method typically includes administering, enterally, an effective amount of the substantially pure population of bacteria, of the composition, or of the foodstuff. Similarly, a method for reducing the effects of a gastrointestinal disease in an animal is provided. Such a method typically includes administering, enterally, an effective amount of the substantially pure population of bacteria, of the composition, or of the foodstuff. Representative animals are humans. In some embodiments, the effective amount is from about $10^2$ CFU/day to about $10^{12}$ CFU/day.

In another aspect, a method of identifying, in vivo, a microbial strain that has a symbiotic relationship with a prebiotic is provided. Such a method typically includes administering at least one dose of the prebiotic to at least one subject; collecting a sample comprising gastrointestinal microbiota from the at least one subject; and identifying one or more microbial strains that are increased in the sample collected from the subject relative to a baseline sample collected from the subject. In some embodiment, the method further includes isolating the one or more microbial strains that are increased in the sample collected from the subject. In some embodiments, the method further includes genotyping the one or more microbial strains that are increased in the sample collected from the subject. In certain instances, the genotyping comprises sequencing the 16S rDNA. Representative prebiotic include, without limitation, GOS, fructooligosaccharide (FOS), and inulin. In some embodiments, the administering step includes administering the prebiotic to the at least one subject in sequentially higher doses over time. In some embodiments, the administering step lasts for at least a week. In some embodiments, the sample is a fecal sample.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Part A

Part B

Figure 4:
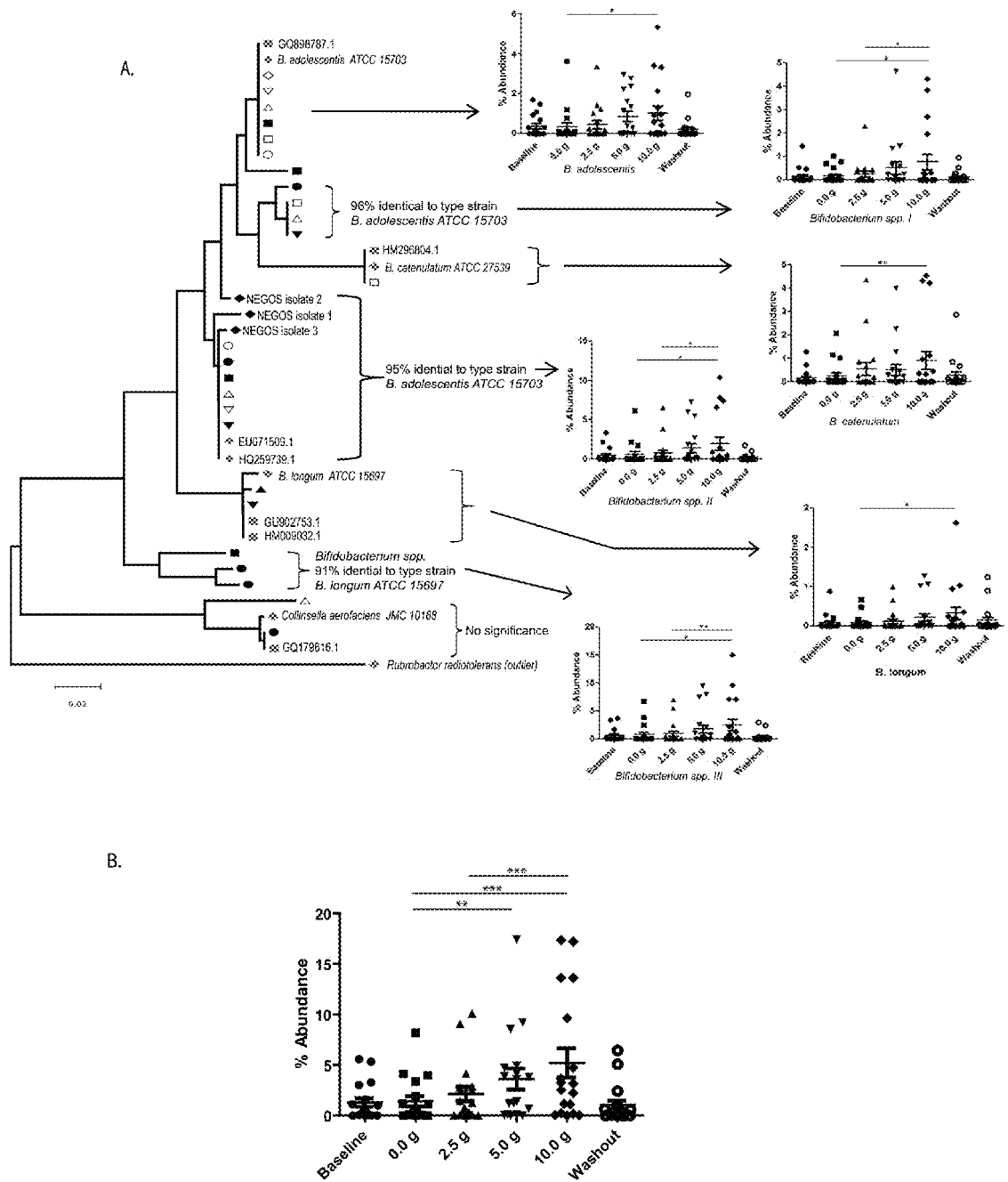

FIG. 4 is a characterization of the fecal microbiota in eighteen subjects that consumed increasing doses of GOS by multiplex pyrosequencing of 16S rDNA tags. A phylogenetic tree that encompasses the phylum Actinobacteria is shown (A). The tree contains representative sequences of all OTUs detected that were significantly affected by GOS in individual subjects together with sequences of related entries in the database. The latter includes both type strains of known species and sequences from molecular studies of human fecal samples. Sequences were aligned using Muscle 3.6 and the trees were constructed using the neighbor-joining algorithm with 1,000 bootstrap replicates in MEGA 4.0. The sequences from individual subjects are labeled using open black and closed black symbols, and type strains and other sequenced human strains are indicated by grey symbols. Those OTUs that were not significantly affected in all eighteen subjects were labeled as "No significance". Graphs to the right of the trees show the abundance of the OTUs and bacterial groups that were significantly affected by GOS. The abundances of all of the *Bifidobacterium* species affected by GOS consumption, for all eighteen subjects, are shown in B. These graphs show mean proportions of the three individual samples taken during the treatment periods for each subject. Baseline and washout refer to samples taken in periods where no GOS was consumed. Repeated measures ANOVA in combination with a Tukey's post-hoc test were performed to indentify differences between treatment and control periods, where *=p<0.05, =p<0.01, and *=p<0.001. Baseline and washout periods were not included in the statistic analysis.

Figure 5:
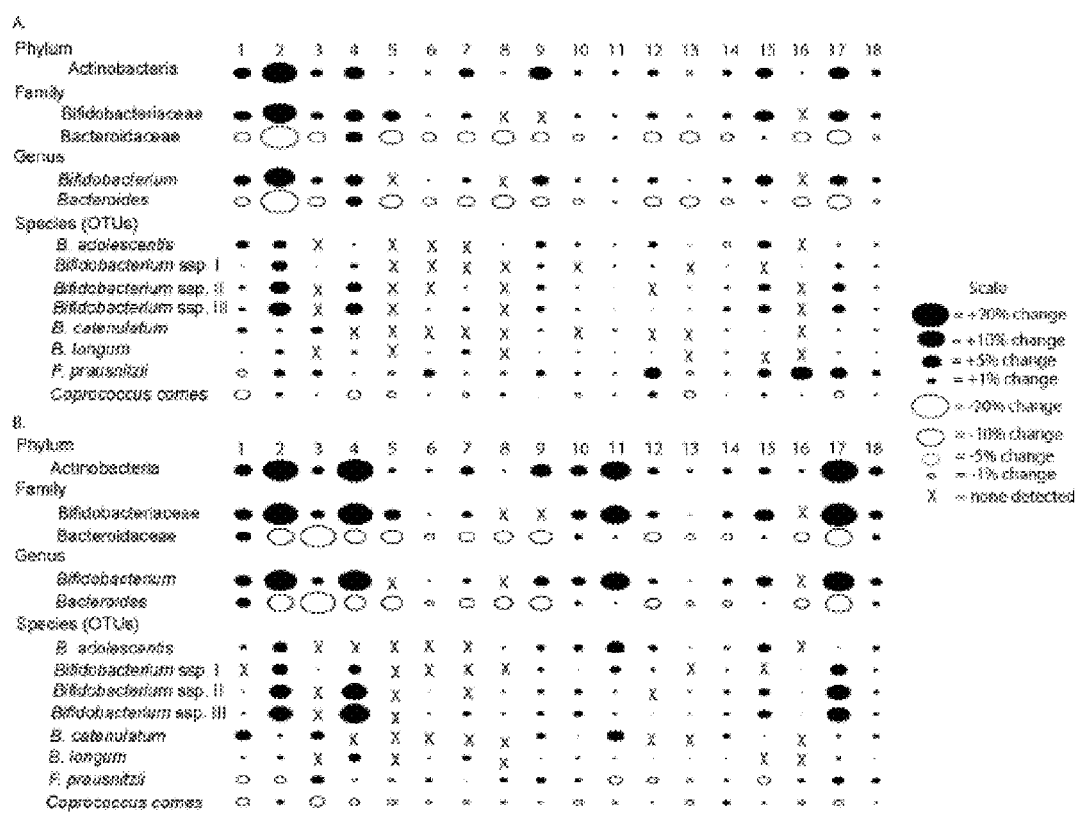

FIG. 5 is a bubble plots showing differences in the proportions of bacterial taxa as a percentage of the entire bacteria population detected during consumption of 5.0 g (A) and 10.0 g (B) when compared to the control period. The size of the bubbles is representative of the percent difference. Black ovals represent increases in proportions observed during the GOS consumption period; white ovals represent decreases.

Figure 6:
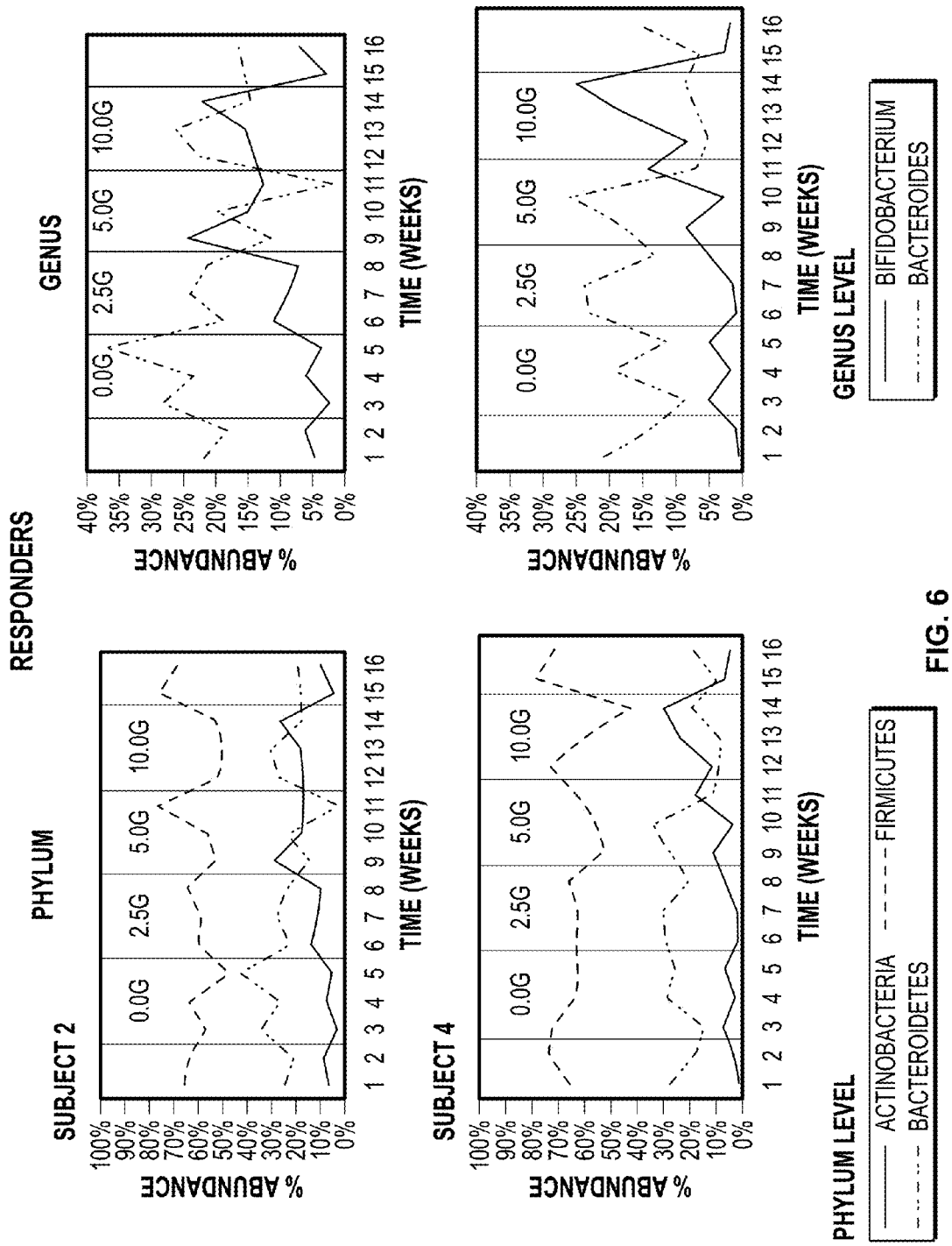
Figure 6:
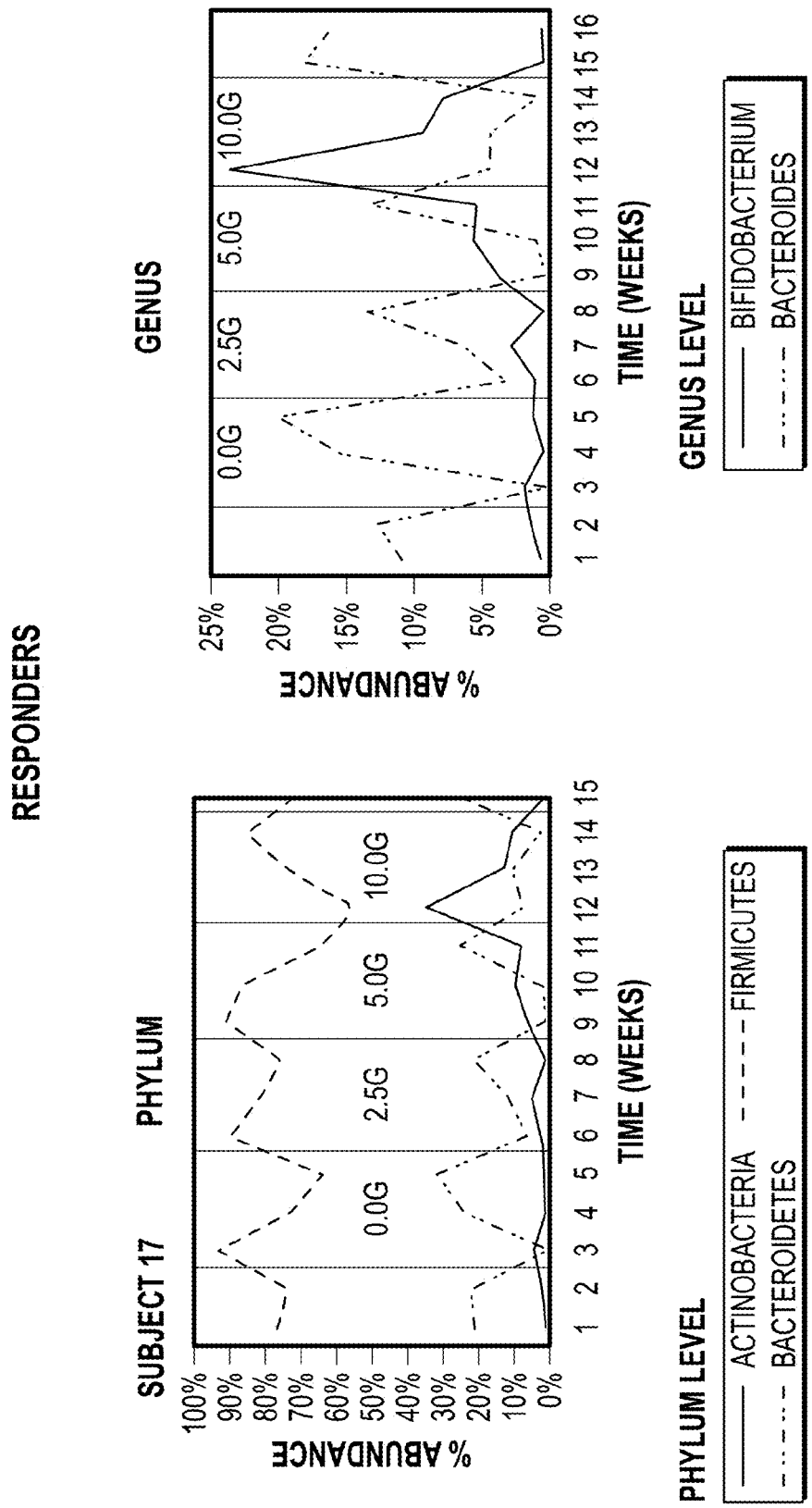
Figure 6:
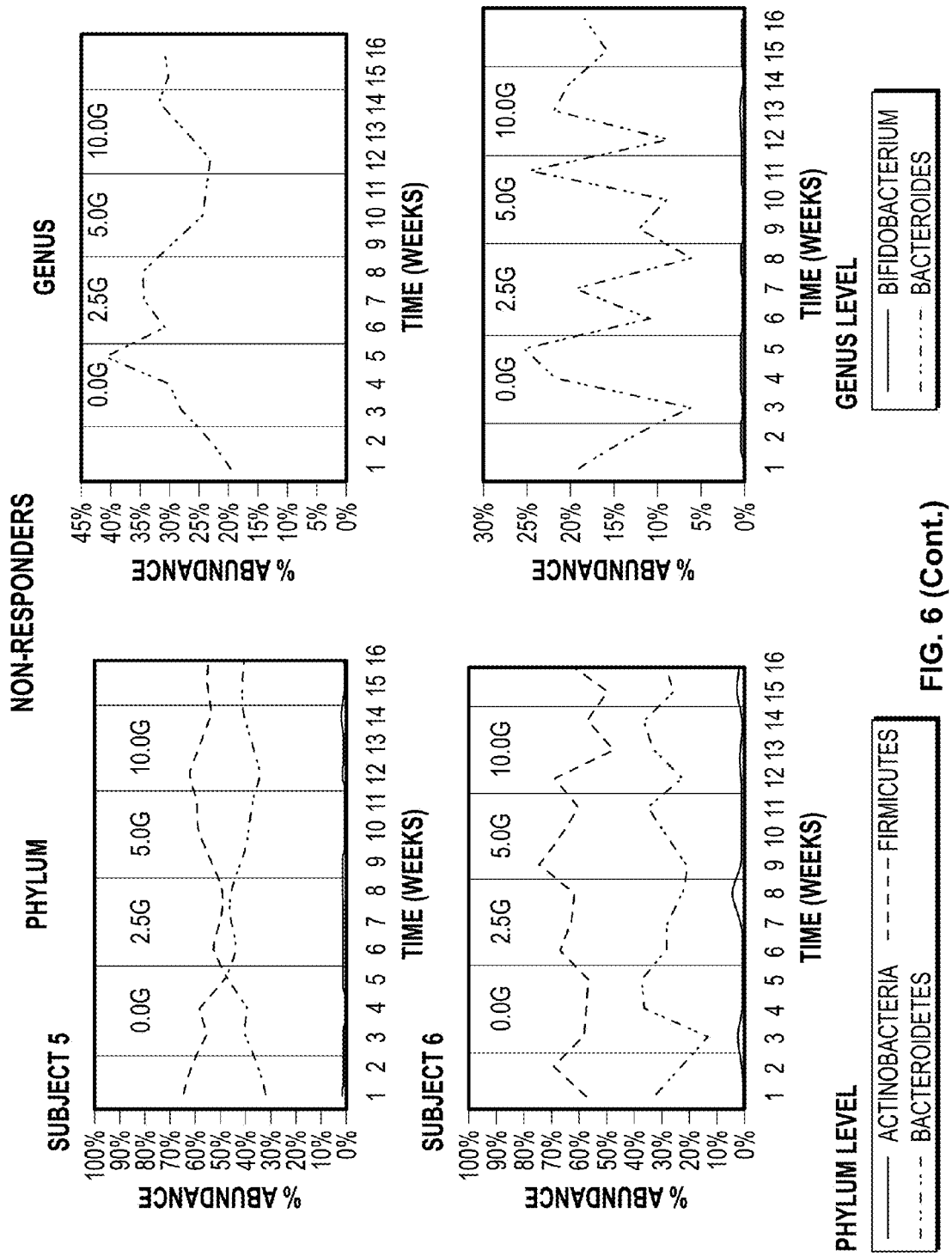

FIG. 6 shows the temporal dynamics of the human fecal microbiota in response to the consumption of increasing doses of GOS shown in five human subjects. Graphs on the left show proportions of the three main phyla (Actinobacteria, Firmicutes, and Bacteroidetes) and two genera (*Bifidobacterium* and *Bacteroides*) that were affected in subjects considered as "responders". Graphs on the right show proportions of the same three phyla and two genera for subjects considered as "non-responders".

Figure 7A:
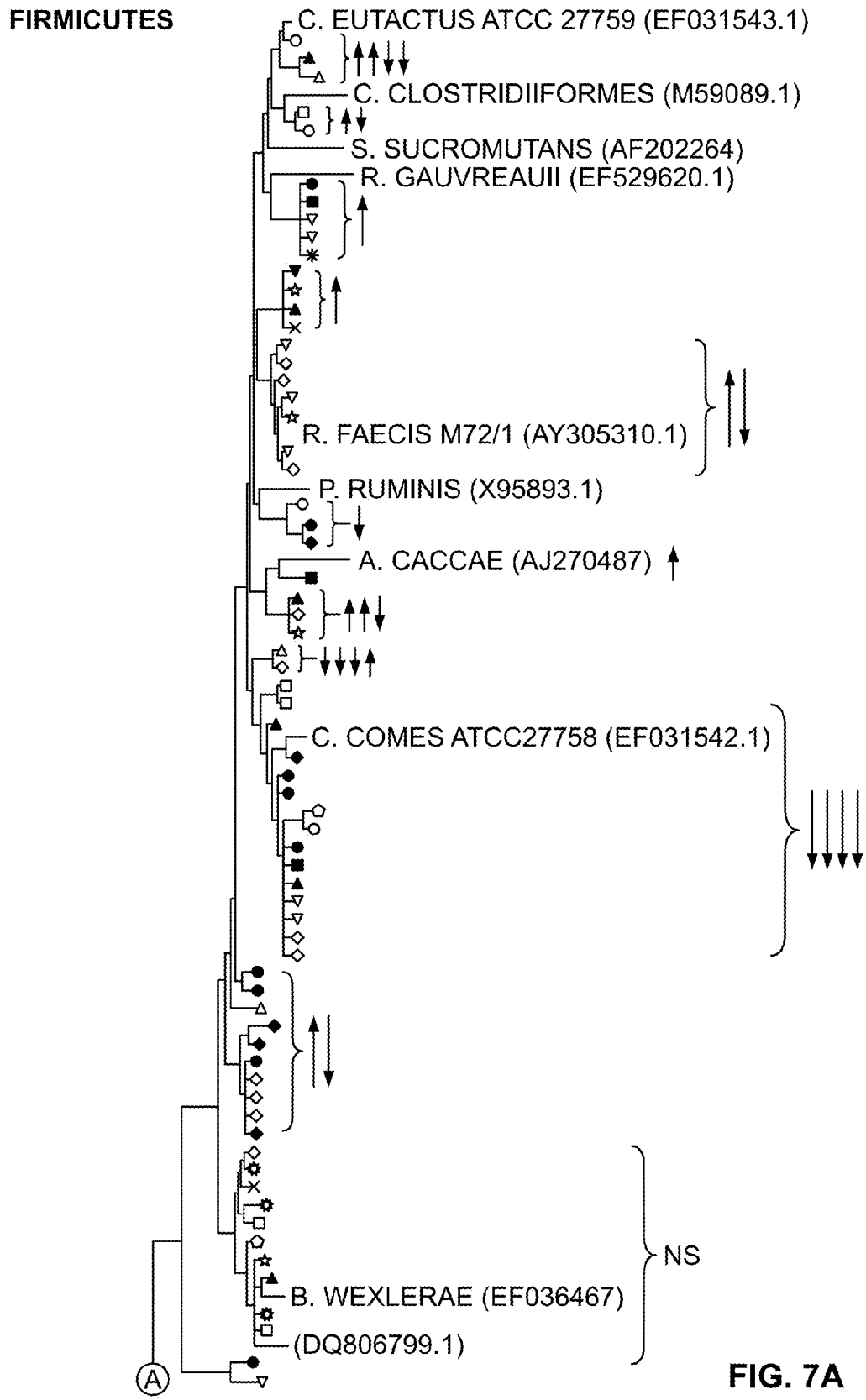
Figure 7A:
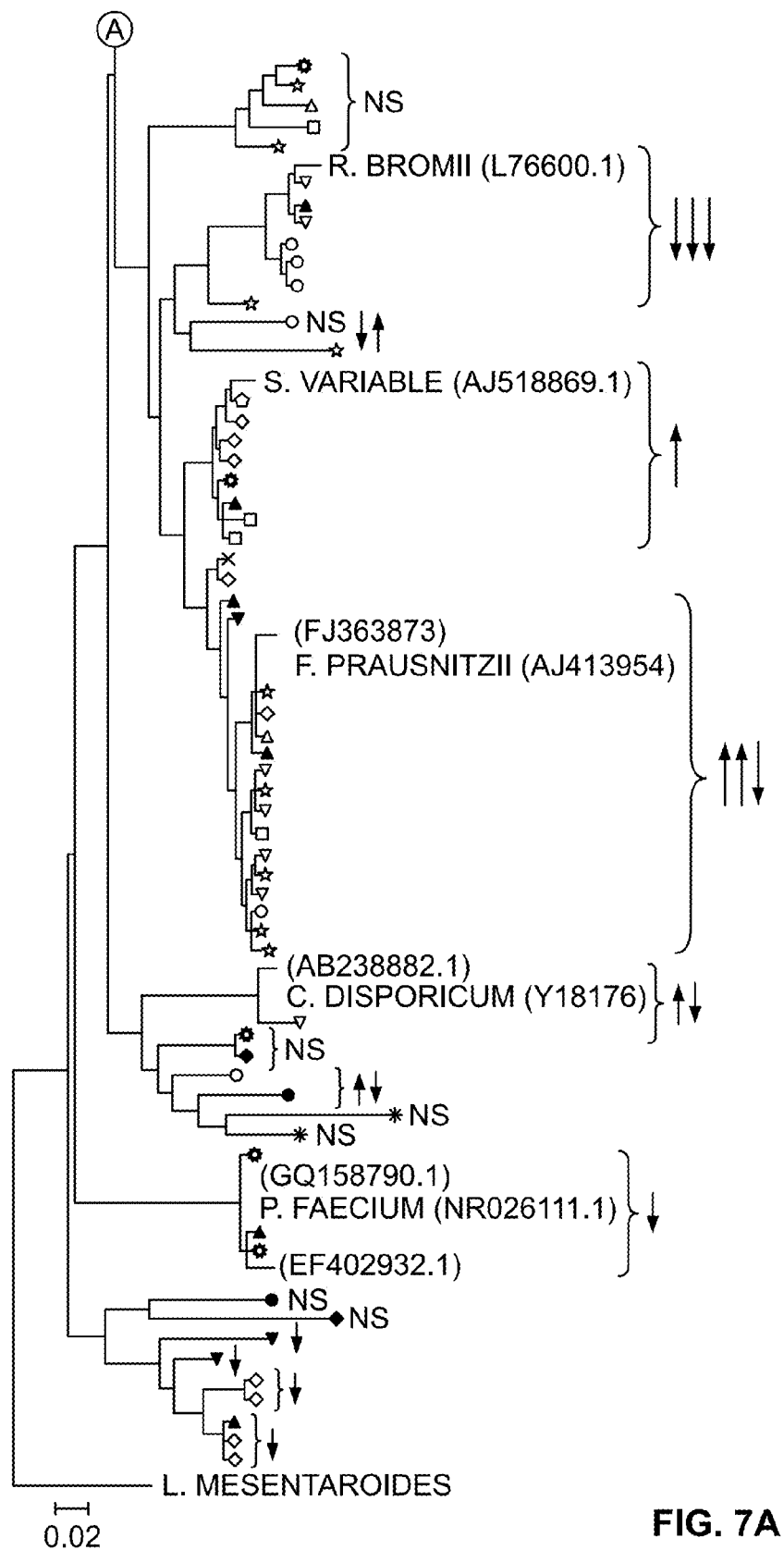

FIG. 7 describes the characterization of the fecal microbiota in eighteen subjects that consumed increasing doses of GOS by multiplex pyrosequencing of 16S rDNA tags. Phylogenetic trees that encompass the phyla, Firmicutes (A) and Bacteroidetes (B) are shown. The trees contain representative sequences of all OTUs that were significantly affected by GOS in individual subjects together with sequences of related entries in the database (which included both type strains of known species and sequences from molecular studies of human fecal samples). Sequences were aligned in Muscle 3.6 and the trees were built using the neighbor joining algorithm with 1,000 bootstrap replicates in MEGA 4.0. Open black, closed black, and grey symbols were used to label sequences from individual subjects. OTUs that were not significantly affected in any of the eighteen subjects were labeled as "NS". Arrows to the right of each cluster indicate the number of subjects that showed statistical significance after ANOVA analysis. The direction of the arrow indicates either a significant increase (↑) or significant decrease (↓) for each subject showing significance for that particular OTU cluster.

Figure 8:
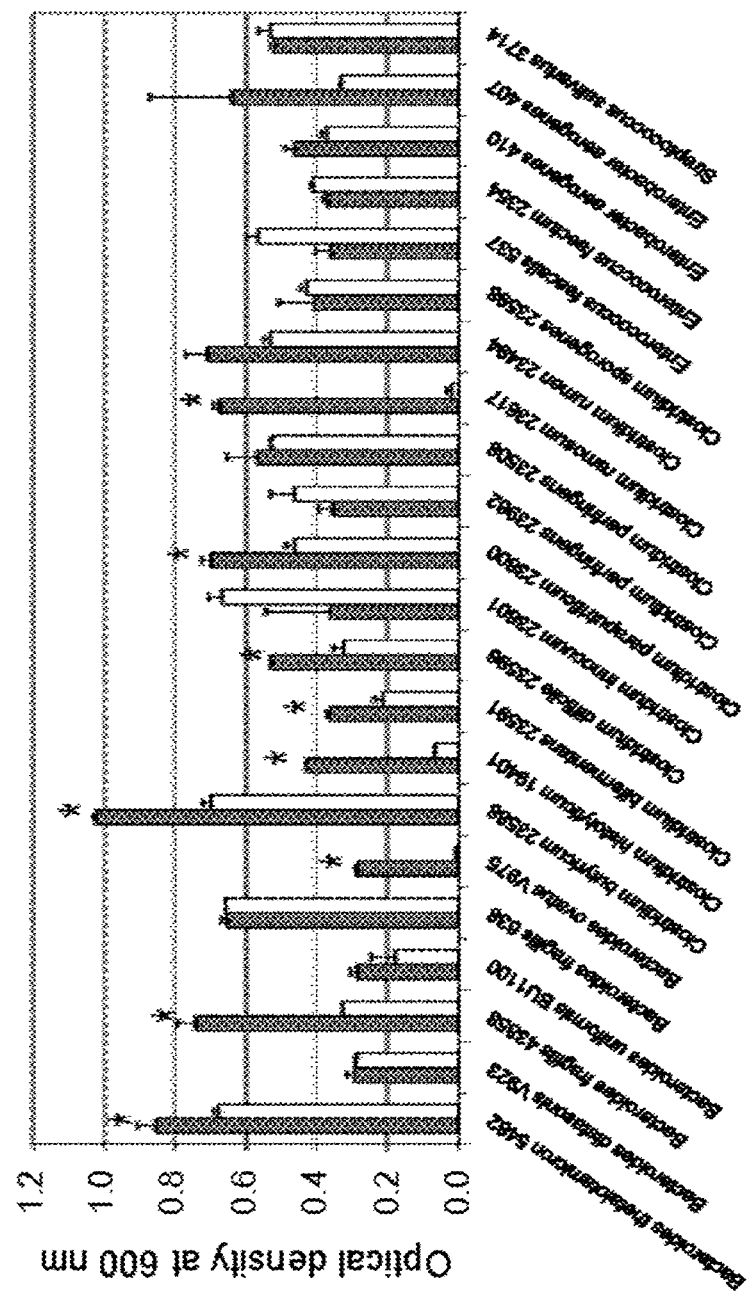

FIG. 8 shows that twenty-two anaerobic bacteria of human gastrointestinal origin were screened in vitro to determine their ability to utilize GOS. Average optical densities and standard deviations for each of the strains are shown, with GOS-grown cultures in shaded bars and control cultures in open bars. Significant differences were determined by students T-test and indicated by asterisks, where p<0.05.

Part C

Figure 9:
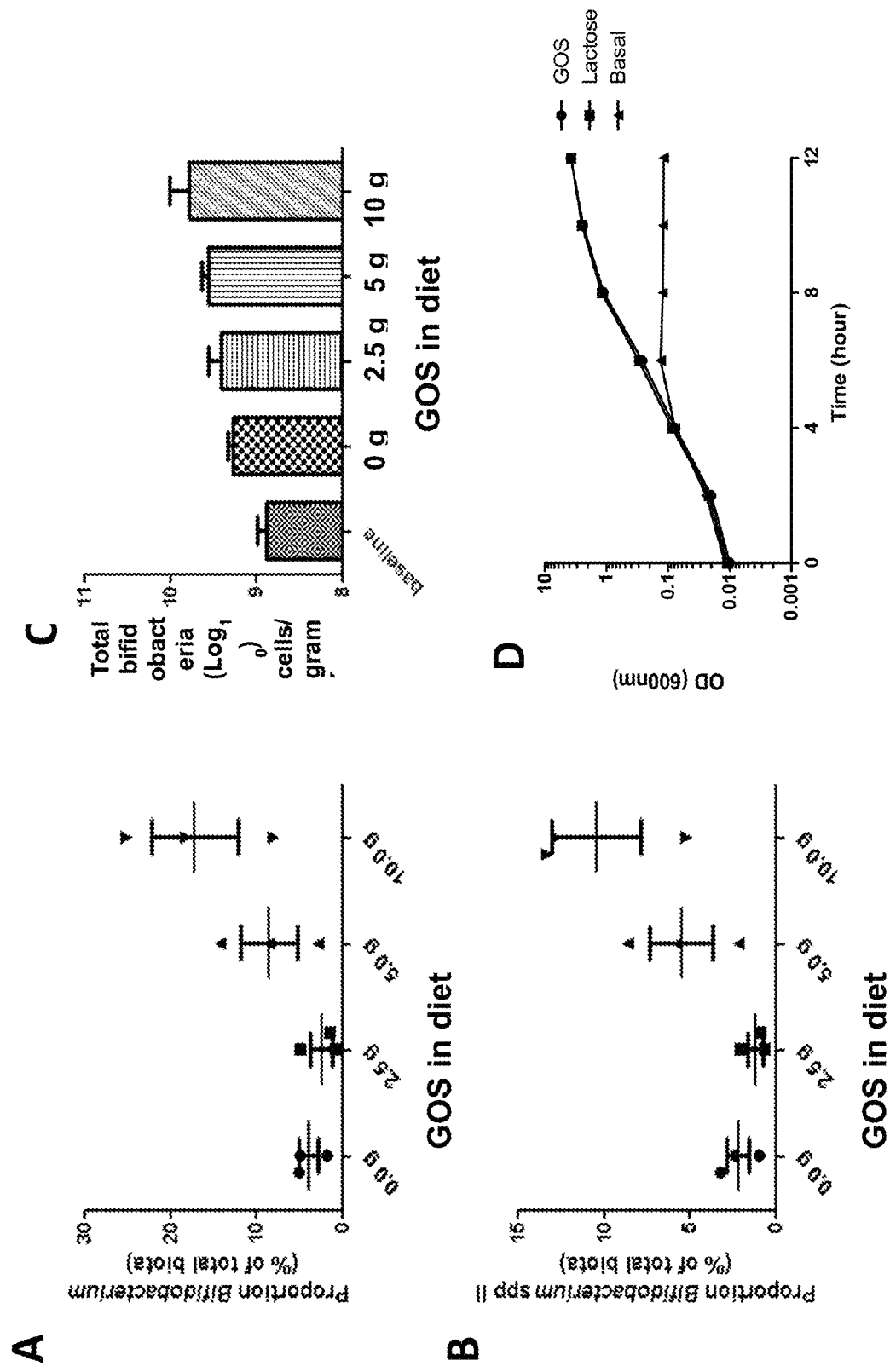

FIG. 9 shows the characterization of the *Bifidobacterium* biota in fecal samples from a human subject consuming GOS and in vitro GOS fermentation of a subsequently isolated *Bifidobacterium* strain. (A) Proportion of bifidobacteria in the fecal microbiota as determined by pyrosequencing. Chews with four increasing doses (0, 2.5, 5, and 10 g) of GOS were consumed in succession, each for three weeks. Analyses of fecal samples collected weekly are shown. (B) Proportion of *Bifidobacterium* lineage spp. II in the same fecal microbiota as determined by pyrosequencing. (C) Total numbers of bifidobacteria in the same fecal samples as determined by qRT-PCR. (D) Growth of *Bifidobacterium adolescentis* BD1 on GOS, lactose, and basal MRS medium without added carbohydrates.

Figure 10:
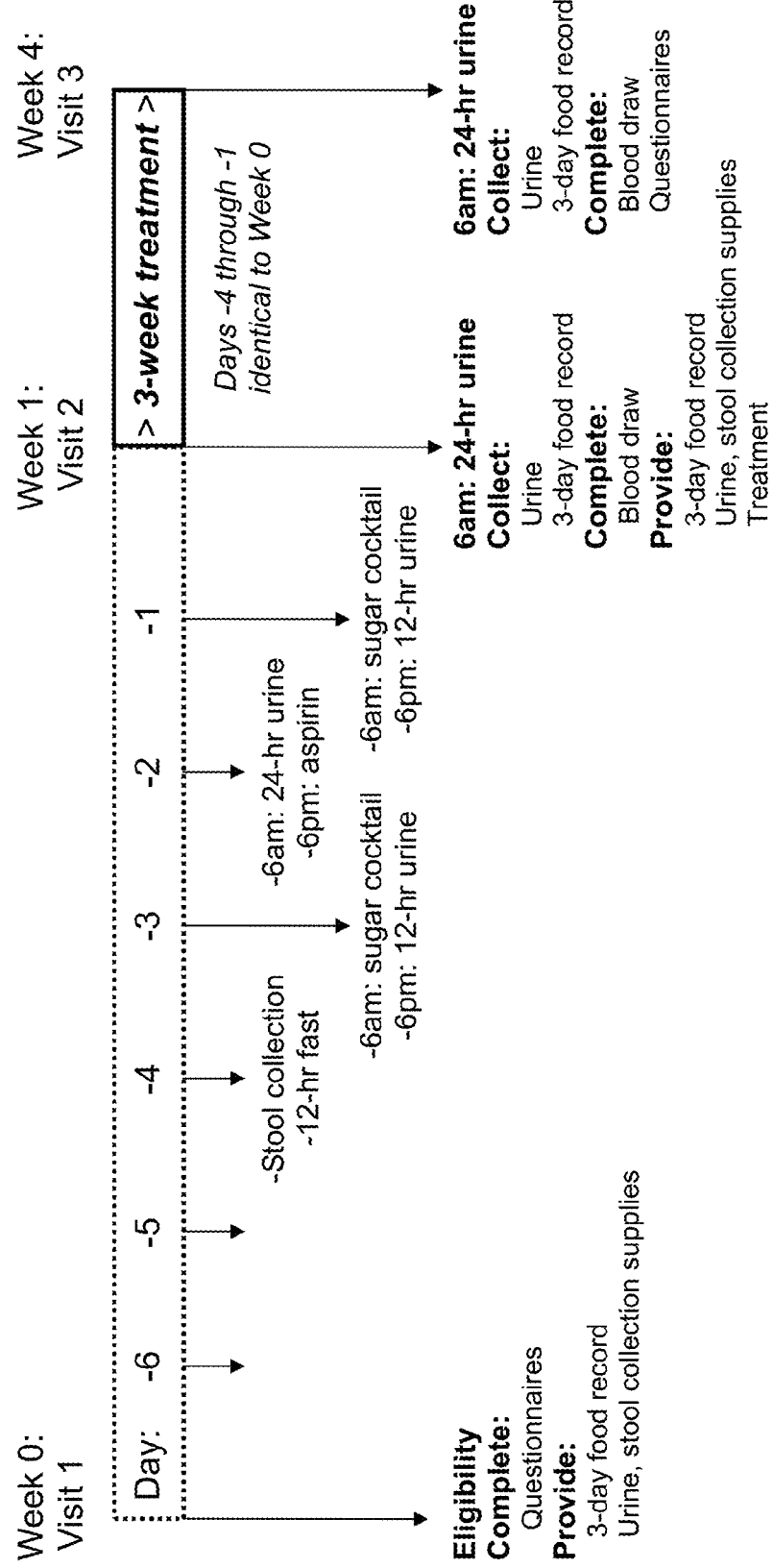

FIG. 10 is a representation of the timeline for stool and urine collection.

DETAILED DESCRIPTION

The present disclosure provides methods of selecting and isolating one or more microbial strains that are naturally occurring in the gastrointestinal microbiota and that exhibit improved characteristics in the presence of a prebiotic. Following isolation and characterization, the in vivo-selected microbial strain can be used as a probiotic and, along with the prebiotic, can be administered as a synbiotic composition to an animal. For purposes herein, gastrointestinal microbiota refers to the microbial population that is present in the gastrointestinal tract of a subject. The gastrointestinal tract typically includes the mouth, esophagus, stomach, small intestine, large intestine, rectum and anus.

As described herein, methods are provided in which a microbial strain that is naturally present in the gastrointestinal microbiota of one or more subjects can be specifically selected for based on its positive response to the presence of a prebiotic. Such methods typically start with the administration of a prebiotic to a subject. As used herein, a subject can refer to a human or a non-human. Representative non-human subjects include, without limitation, livestock (e.g., swine, cow, horse, goat, and sheep), poultry (e.g., fowls such as chicken and turkey), and companion animals (e.g., pets such as dogs and cats).

Prebiotics are defined in the art as an "ingredient that allows specific changes, both in the composition and/or activity in the gastrointestinal microbiota that confers benefits upon host well-being and health" (see, for example, Roberfroid, 1998, Br. J. Nutr., 80:S197-202). Well characterized prebiotics include, for example, galacto-oligosaccharide (GOS), fructooligosaccharide (FOS), and inulin. GOS and FOS refer to a group of oligomeric, non-digestible carbohydrates that are produced from lactose using beta-galactosidases to catalyze transgalactosylation reactions. These beta-linked glycosides are recalcitrant to digestion by host-secreted enzymes in the small intestine, such that they reach the colon intact and are available to the colonic microbiota. It would be understood by those skilled in the art that other compounds that fall within the definition of a prebiotic also can be used in the methods described herein.

Typically, a subject is administered (e.g., asked to ingest) at least one dose of the prebiotic but, more often, a number of doses over a period of time (e.g., one or more doses per day for multiple days (e.g., for about or at least a week, for about or at least two weeks)). In some instances, to help or further validate the correlation between an increase in a microbial strain and the presence of a prebiotic, the subject can be administered (e.g., asked to ingest) a prebiotic in sequentially higher doses over time.

At selected points while the subject is ingesting the prebiotic, samples that contain gastrointestinal microbiota are collected from the subject. In most instances, the sample is a fecal sample, but other samples, provided they contain gastrointestinal microbiota, are suitable for use in the methods described herein (e.g., an enema wash, a sample taken during a colonoscopy). It would be understood by those skilled in the art that, for comparison purposes, at least one baseline sample needs to be obtained from each subject. As used herein, a baseline sample refers to a sample that is taken or obtained from the subject before any prebiotic is ingested or following a sufficient time period after the prebiotics are no longer ingested. Obviously, multiple baseline samples can be obtained from the same subject.

Of particular interest are the microbial strains that increase in the presence of the prebiotic compared to, for example, one or more baseline samples. Standard laboratory methodologies are routinely used to identify the genera that are present in the gastrointestinal microbiota. These methods can include gram staining, differential culture conditions (e.g., utilizing different culture media under aerobic/anaerobic conditions at different, temperatures), immunological assays, and/or MALDI-TOF. In addition, routine laboratory methodologies can be used to isolate one or more microbial strains that are increased in a subject in the presence of the prebiotic. As used herein, "isolated" refers to a population of microbial cells in which at least about 80% (e.g., about 85%, 90%, 95%, 99% or 100%) of the cells are the *B. adolescentis* BD1 strain described herein.

In some instances, following the culture methods of identification, one or more methods of genotyping can be used to further confirm the genus and/or genus and species of one or more microbial strains. Because they are extremely highly conserved, the genes encoding the rRNA sequences (rDNA) are routinely used to determine taxonomy as well as phylogeny and rate of divergence. For example, PCR with restriction fragment length polymorphism (RFLP) of the 16S rDNA can be used to genotype microorganisms (see, for example, Urakawa et al., 1997, *FEMS Microbiol. Lett.*, 152:125-32), sequencing of the 16S rDNA can be used to genotype microorganisms (see, for example, Weisburg et al., 1991, *J. Bacteriol.*, 173:697-703), or mass spectroscopy of cleaved 16S rDNA or rRNA can be used to genotype microorganisms (see, for example, Jackson et al., 2006, *BMC Bioinformatics*, 7:321). These methods are routinely used in microbiology and are continually being modified and improved upon; the methods described herein are not to be limited by any particular methods used to genotype microorganisms.

Using the methods described herein, a microbial strain can be identified, based on in vivo selection, that increases in number or otherwise responds positively to the presence of a prebiotic. In addition to an increase in number of one or more microbial strains in the presence of a prebiotic relative to a baseline sample, a "positive response" can refer to, for example, an increase in metabolic activity by the microbial strain (i.e., in the absence of an increase in number) or both an increase in number and an increase in metabolic activity.

As described herein, this method has been used to identify a microbial strain that responds particularly well in a number of subjects to the prebiotic, GOS. This microbial strain was identified as a *Bifidobacterium adolescentis* strain, and was assigned the designation BD1. This strain was deposited with the American Type Culture Collection (ATCC, 10801 University Blvd., Manassas, Va. 20110) on Oct. 8, 2013, and assigned Accession No. PTA-120614.

The *B. adolescentis* BD1 strain or other strains identified using the methods herein can be provided as a substantially pure population. As used herein, a "substantially pure population" of cells means that at least about 50% (e.g., about 55%, 60%, 65%, 70%, 75%, 80% or greater) of the cells present are the *B. adolescentis* BD1 strain described herein. Methods of culturing *B. adolescentis* are well known to those of skill in the art. See, for example, Handbook of Culture Media for Food Microbiology, $2^{nd}$ Ed., Vol 37, Corry et al., eds., 2003, Elsevier Science. In addition, there is a commercially available selective medium defined specifically for culturing *Bifidobacterium* (e.g., BD *Bifidobacterium* Agar from Becton, Dickinson & Co.).

After selecting, identifying and isolating a microbial strain using the methods disclosed herein, and after confirming the microbial strains affinity for the prebiotic, the microbial strain can be administered to an animal (e.g., as a probiotic). Given the method by which the microbial strain was obtained, it is preferred that the microbial strain be administered to an animal in conjunction with the corresponding prebiotic. In some embodiments, the microbial strain and the prebiotic are combined prior to administration to produce a symbiotic. Typically, the animal that is administered the rationally-designed synbiotic is of the same species as the subject from which the microbial strain originally was identified. As described above with respect to the subjects, the animal can be a human or any number of non-human animals.

In some embodiments, the microbial strain and the prebiotic (e.g., the synbiotic) can be contained within a foodstuff. Foodstuffs include any number of food products that are suitable for human consumption such as, without limitation, milk, yogurt, juices, water, cereals, chewing gum, crackers, candies, cookies, vitamin supplements, meats, and fruits or vegetables (i.e., blended fruits or vegetables such as, e.g., baby food). Foodstuffs also include feed products (e.g., suitable for consumption by livestock or companion animals) including dry animal feeds. In certain embodiments, the *B. adolescentis* microbial strain described herein along with GOS can be mixed into liquid feed or drinking water, or combined with a carrier and applied to solid feed.

A composition or a foodstuff that includes the microbial strain (e.g., *B. adolescentis* BD1) and the prebiotic (e.g., GOS) as described herein can include a pharmaceutically acceptable carrier. A pharmaceutically acceptable carrier should be non-toxic to the bacteria and to the animal, and also can include an ingredient that promotes viability of the microorganism during storage. Liquid or gel-based carriers are well known in the art, such as water, fruit juice, glucose or fructose solutions, physiological electrolyte solutions, and glycols such as methanol, ethanol, propanol, butanol, ethylene glycol and propylene glycol. Carriers also include oleaginous carries such as, for example, white petrolatum, isopropyl myristate, lanolin or lanolin alcohols, mineral oil, fragrant or essential oil, nasturtium extract oil, sorbitan mono-oleate, cetylstearyl alcohol, hydroxypropyl cellulose (MW=100,000 to 1,000, 000), or detergents (e.g., polyoxyl stearate or sodium lauryl sulfate). Other suitable carriers include water-in-oil or oil-in-water emulsions and mixtures of emulsifiers and emollients are provided.

A composition or a foodstuff that includes the microbial strain (e.g., *B. adolescentis* BD1) and the prebiotic (e.g., GOS) as described herein also can include natural or synthetic flavorings and food-quality coloring agents, thickening agents such as corn starch, guar gum, xanthan gum and the like, binders, disintegrators, coating agents, lubricants, stabilizers, solubilizing agents, suspending agents, excipients, and diluents. Additional components also can be included that, for example, improve palatability, improve shelf-life, and impart nutritional benefits. It would be understood by those in the art that any additional components in a composition must be compatible with maintaining the viability of the microbial strain.

Administration of a composition or a foodstuff that includes the microbial strain (e.g., *B. adolescentis* BD1) and the prebiotic (e.g., GOS) as described herein can be accomplished by any method that delivers at least a portion of the microorganisms and prebiotic into the digestive tract of an animal. Therefore, enteral administration is preferred (e.g., orally, sublingually, or rectally), although other routes are not excluded. Generally, the formulation of a composition is dependent upon its intended route of delivery. For example, a composition that includes the *B. adolescentis* BD1 strain (with or without GOS) as described herein can be formulated as a powder, a granule, a tablet, a capsule, a liquid suspension, a paste, or a syrup.

An effective amount of the microbial strain (i.e., a probiotic) described herein is an amount that achieves a desired result (e.g., treatment or maintenance) in the absence of a toxic, immunological, or allergic reaction in the animal. An effective amount can be at least $10^4$ viable colony forming units per day (CFU/day; e.g., at least $10^6$ CFU/day, $10^8$ to $10^{12}$ CFU/day, or $10^{10}$ CFU/day), which can be administered in a single dose or over multiple doses (e.g., over days, weeks, months or years). When the microbial strain described herein is administered over a long period of time (e.g., to maintain a healthy gastrointestinal flora), the effective amount may be less than the foregoing range (e.g., 10 CFU/day to $10^3$ CFU/day). It would be understood by those in the art that the Bifidobacteria strain described herein can be administered in an amount that exceeds the foregoing range as many Bifidobacteria strains are considered to be highly safe and have been given GRAS (Generally Recognized As Safe) status by the U.S. Food and Drug Administration (FDA). It would be appreciated by those skilled in the art that, in the presence of the prebiotic, the effective amount (i.e., the amount that achieves a desired result) may be reduced and/or the therapeutic effect may be increased with the same or less amount.

Probiotics are reported to produce health benefits which include (1) alleviation of intestinal disorders such as constipation and diarrhea caused by infection by pathogenic organisms, antibiotics, or chemotherapy; (2) stimulation and modulation of the immune system; (3) anti-tumor effects due to inactivation or inhibition of carcinogenic compounds in the gastrointestinal tract by reduction of intestinal bacterial enzyme activities such as beta-glucuronidase, azoreductase, and nitroreductase; (4) reduced production of toxic end products such as ammonia, phenols and other metabolites of protein known to influence liver cirrhosis (5) reduction in serum cholesterol and blood pressure; (6) maintenance of mucosal integrity; (7) alleviation of symptoms of lactose intolerance; (8) prevention of vaginitis. Accordingly, the beneficial effects attributed to probiotics include increased resistance to infectious diseases, healthier immune systems, reduction in irritable bowel syndrome, reductions in blood pressure, reduced serum cholesterol, milder allergies and tumor regression. In animals, for example, probiotics can enhance weight gain or weight loss and improve meat quality, and milk production. Significantly, probiotics can be used to establish and maintain a healthy (e.g., balanced) gastrointestinal flora in an animal and to reduce the effect of gastrointestinal diseases. Gastrointestinal diseases include, without limitation, diarrhea, constipation, loose stool, abdominal inflation, ulcerous colitis, Crohn's disease, irritable bowel syndrome, hypersensitive intestinal syndromes, food toxicity, food allergy, pseudomembranous colitis, hemorrhagic colitis, gastritis, gastroduodenal ulcer, dental caries, and periodontitis. See, for example, Vaughan, *Gastrointestinal Microbiology*, 2006, CRC Press. Specifically, Bifidobacteria may prevent or reduce the effects of metabolic disorders such as obesity and type 2 diabetes by reducing gut permeability. Reducing gut permeability can improve metabolic endotoxemia and metabolic inflammation, both of which are involved in obesity and related metabolic disorders.

In some embodiments, the microbial strain described herein, with or without a prebiotic, can be administered with one or more additional probiotic microbial strains. Examples of additional probiotic microorganisms that can be used include yeasts such as *Saccharomyces*, *Candida*, *Pichia* and *Torulopsis*, moulds such as *Aspergillus*, *Rhizopus*, *Mucor*, and *Penicillium* and bacteria such as the genera *Lactobacillus*, *Bifidobacterium*, *Clostridium*, *Leuconostoc*, *Bacteroides*, *Staphylococcus*, *Lactococcus*, *Bacillus*, *Streptococcus*, *Fusobacterium*, *Propionibacterium*, *Enterococcus*, *Pediococcus*, and *Micrococcus*. Representative examples of additional probiotic microorganisms that can be used include *Saccharomyces cereviseae*, *Bacillus coagulans*, *Bacillus licheniformis*, *Bacillus subtilis*, *Bifidobacterium bifidum*, *Bifidobacterium infantis*, *Bifidobacterium longum*, *Enterococcus faecium*, *Enterococcus faecalis*, *Lactobacillus acidophilus*, *Lactobacillus alimentarius*, *Lactobacillus casei*, *Lactobacillus curvatus*, *Lactobacillus delbruckii*, *Lactobacillus johnsonii*, *Lactobacillus farciminus*, *Lactobacillus gasseri*, *Lactobacillus helveticus*, *Lactobacillus rhamnosus*, *Lactobacillus sake*, *Lactococcus lactis*, *Micrococcus varians*, *Pediococcus acidilactici*, and *Staphylococcus xylosus*.

The microbial strain described herein can be provided in an article of manufacture (e.g., in lyophilized form), with or without a prebiotic. An article of manufacture also can include one or more pharmaceutically acceptable carriers (e.g., a solvent), and further can include one or more tools for combining and mixing the microorganism with the prebiotic and/or the pharmaceutically acceptable carrier or administering the composition (e.g., a stick or a straw). In addition, an article of manufacture can include one or more other probiotic microorganisms. An article of manufacture also can include appropriate packaging material, and may include written directions or instructions for use (e.g., dosage information) or for administration.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Part A

Example 1

Preparation of Chocolate Chews

Chocolate-flavored chewable candies (chews) containing GOS and control chews (with no GOS) were prepared at the University of Nebraska-Lincoln Food Processing Center. The GOS used was Purimune™, a high purity GOS powder (91.8% on a dry basis) provided by GTC Nutrition (Golden, Colo.). The balance of the GOS contained lactose (7%), glucose (<1%), and galactose (<0.5%). The chocolate chews were formulated to contain 1.25 g of GOS per 6 g chew. Additional corn syrup and sucrose were included in the control chews containing no GOS. The formulations of both the GOS and control chew are shown in Table 1. Chews were wrapped individually in wax paper and stored in sealed plastic bags at 20° C. The chews were distributed to subjects on a weekly basis.

TABLE 1

| Ingredient | Control chocolate chew | GOS chocolate chew |
| --- | --- | --- |
| Water | 11.62 | 11.54 |
| Sugar | 27.35 | 19.42 |
| GOS (Purimune) | 0.00 | 23.40 |
| Corn syrup | 44.84 | 31.83 |
| Palm Kernel oil | 7.62 | 5.41 |
| Chocolate liquor (1/2 bakers) | 7.58 | 7.44 |
| Lecithin | 0.55 | 0.53 |
| Vanilla | 0.44 | 0.43 |

Example 2

Experimental Design

The study included 21 healthy human volunteer subjects that were recruited on the University of Nebraska-Lincoln campus. None of the subjects had been on antibiotics or on a vegetarian diet within three months prior to the start of the study or during the study. Subjects were allowed to maintain their normal lifestyles without any additional restrictions on their diets. Two subjects dropped out of the study for reasons unrelated to the experiment and one subject was released from the study due to pregnancy. Thus, a total of eighteen subjects, 13 males and 5 females, between the ages of 19 and 50 years old, completed the study. The study was conducted over a 16 week period. A two-week baseline period (no chews administered) was conducted at the beginning of the study, followed by four sequential testing periods during which chews were administered for three weeks with GOS dosages at levels of 0.0 g, 2.5 g, 5.0 g, and 10.0 g GOS per day. Subjects were blinded in terms of the dose of GOS they received, and instructed to consume eight chews per day during each testing period, with the only difference being the number of GOS-containing chews included in the daily regimen, which could not be differentiated from control chews. Thus, during the control period, 8 control chews were consumed, and during the 2.5 g treatment period, 2 GOS chews (each containing 1.25 g GOS) and 6 control chews were consumed. The 5 g treatment period included 4 GOS and 4 control chews and the 10 g treatment consisted of 8 GOS chews. A final two-week washout period (no chews) was performed at the end of the fourth testing period. All of the dosages were sequential with no washout periods between dosages. Subjects were asked to report the presence, absence, and severity of gastrointestinal symptoms experienced throughout each week of the study. The symptoms survey was based on previously reported studies (Bouhnik et al., 1997, *Am. J. Clin. Nutr.*, 69:980-91; Bouhnik et al., 2004, *Am. J. Clin. Nutr.*, 80:1658-64; and Shadid et al., 2007, *Am. J. Clin. Nutr.*, 86:1426-37) and included bowel movement, stool consistency, discomfort, flatulence, abdominal pain, and bloating, and were scored on a one (none, normal, good well-being) to five (severe symptoms and discomfort) scale provided as part of weekly subject diaries. The study was approved by the Institutional Review Board of the University of Nebraska.

Example 3

Collection and Processing of Fecal Samples

Fecal samples were collected weekly from each subject. Each sample was processed within 1 hour of a bowel movement. All fecal samples (1.0 g) were weighed and diluted 10-fold with sterile phosphate buffered saline (PBS; pH 7.0). Samples were homogenized and immediately frozen at −80° C. and saved for DNA extraction. Fecal samples (1.0 g) were also immediately introduced into an anaerobic chamber (Bactron IV Anaerobic Chamber, Shel Lab, Cornelius, Oreg.) and a 10-fold dilution series was made with pre-reduced sterile saline (0.9% NaCl). Aliquots were plated on Brain Heart Infusion Agar (Becton Dickinson; BD, Franklin Lakes, N.J.) for total anaerobes (incubated 48 h), Rogosa SL (BD) for *Bifidobacterium* (96 h), and *Bacteroides* Bile Esculine Agar (BD) for *Bacteroides* (48 h). All plates were incubated anaerobically at 37° C. In addition, the Rogosa SL agar plates that were used to enumerate bifidobacteria were also examined at 48 h to estimate *lactobacilli* levels. Serial dilutions were also used to plate aliquots aerobically on MacConkey Agar (BD) for enterobacteria (24 h), and Bile Esculin Azide Agar (Acumedia, USA) for enterococci (48 h). Plates were incubated aerobically at 37° C. These organisms were chosen for cultural enumeration based on previous prebiotic and probiotic feeding studies (Tannock et al., 2000, *Appl. Environ. Microbio.*, 66:2578-88; Tannock et al., 2004, *Appl. Environ. Microbio.*, 70:2129-36).

The fecal pH was measured in aqueous slurries using an Ag/AgCl pH meter (Accumet Basic AB15 pH meter, Fisher Scientific). Statistical analysis was completed using a one-way ANOVA as well as Tukey's post-hoc pair-wise comparison test.

Example 4

DNA Extraction

A 1 mL aliquot of a 1:10 diluted fecal sample in PBS was transferred to sterile bead beating tubes (Biospec products, Bartlesville, Okla.) containing 300 mg of zirconium beads (0.1 mm). Fecal cells were washed three times in chilled PBS using centrifugation at 6,000×g for 5 min. Pellets were resuspended in 100 μL of lysis buffer (200 mM NaCl, 100 mM Tris, 20 mM EDTA, 20 mg/mL Lysozyme, pH 8.0) and incubated at 37° C. for 30 min. Buffer ASL (1.6 mL) from the QIAamp DNA Stool Mini Kit (Qiagen, Hilden, Germany) was added to each sample after the samples were homogenized in a MiniBeadbeater-8 (BioSpec Products, OK, USA) for two min at maximum speed. The DNA was purified from the supernatants using the QIAamp DNA Stool Mini Kit, following the Qiagen kit manufacturer's instructions.

Example 5

Quantitative Real Time-PCR

Quantitative real time PCR (qRT-PCR) was performed as previously described (Martinez et al., 2009, *Appl. Environ. Microbiol.*, 75:4175-84) using a Mastercycler Realplex2 (Eppendorf AG, Hamburg, Germany) with *Bifidobacterium*-specific primers F: 5'TCG CGT C(C/T)G GTG TGA AAG'3

(SEQ ID NO:1) and R: 5'CCA CAT CCA GC(A/G) TCC AC'3 (SEQ ID NO:2; Martinez et al., 2009, supra; Rinttila et al., 2004, J. Appl. Microbiol., 97:1166-77), with an amplicon size of 243 bp. Standard curves for absolute quantification of bifidobacteria in the fecal samples were prepared using overnight cultures (14 h) of *Bifidobacterium animalis* ATCC 25527T and *Bifidobacterium infantis* ATCC 15697T. For each qRT-PCR experiment, a standard curve was prepared, in duplicate, using DNA extracted from cultures at concentrations ranging from 105-108 CFU/mL. Correlation coefficients for all standard curves were above 0.95.

Example 6

Analysis by PCR-DGGE

PCR-DGGE was performed as described (Martinez et al., 2009, supra). Briefly, the V3 region of the 16S rRNA gene was amplified by PCR using universal primers PRBA338fGC (5'CGC CCG CCG CGC GCG GCG GGC GGG GCG GGG GCA CGG GGG GAC TCC TAC GGG AGG CAG CAG'3; SEQ ID NO:3) and PRUN518r (5'ATT ACC GCG GCT GCT GG'3; SEQ ID NO:4) (Ovreas et al., 1997, Appl. Environ. Microbio., 63:3367-73). Denaturing Gradient Gel Electophoresis (DGGE) was performed as described previously (Walter et al., 2000, Appl. Environ. Microbio., 66:297-303), using a DCode universal mutation detection system (Bio-Rad, Hercules). Band fragments of interest were excised, repeatedly purified (Walter et al., 2001, Appl. Environ. Microbio., 67:2578-85), and then cloned using the TOPO® TA Cloning® Kit for Sequencing (pCR® 4 TOPO® Vector) (Invitrogen). The QIAprep Spin Miniprep Kit (Qiagen, Hilden, Germany) was used to isolate plasmids from transformants, and inserts were sequenced by a commercial provider. Closest relatives of the partial 16S rRNA sequences were determined using the SeqMatch web tool provided through the Ribosomal Database Project (rdp.cme.msu.edu on the World Wide Web).

BioNumerics software Version 5.0 (Applied Maths) was used to analyze DGGE profiles. DGGE bands were automatically assigned and densitometric curves were obtained based on the staining intensity profiles generated by the BioNumerics software. Band staining intensities were calculated as a percent of each peak area of the entire fingerprint generated for the individual sample. The reliability of this quantification method was previously determined by comparing taxa abundance inferred by DGGE band intensities with those obtained with pyrosequencing of 16S rRNA tags in studies on the hamster microbiota, and received correlations of r>0.8 (Martinez et al., 2009, supra).

Example 7

Statistical Analysis

One-way ANOVA tests with repeated measures were used to determine significance between the different doses of GOS (0, 2.5 g, 5 g, and 10 g) and the control. Baseline/washout samples were combined for the analysis and referred to as "none". Statistical analysis was performed for the combined data from the eighteen subjects and to identify statistically significant increases of individual subjects. Tukey's test was used for post hoc pair-wise comparisons.

Example 8

Digestive Tolerance of GOS

All eighteen subjects completed a weekly symptoms diary throughout the duration of the study. These symptoms diaries allowed subjects to rate bowel movement, stool consistency, discomfort, flatulence, abdominal pain, and bloating on a scale of one (none, normal, good well-being) to five (severe symptoms and discomfort). Based on a one-way ANOVA of the data, no significant differences were detected for any of the symptoms between the 0.0 g GOS control dose and any of the GOS treatments (Table 2). A significant symptom change was observed for flatulence ($p<0.05$), but only between the baseline and washout and the treatment periods. However, the increase in this score occurred not only for the GOS treatments, but even during consumption of the 0.0 g GOS control period.

TABLE 2

Mean ± standard deviations of weekly symptoms.
Reported on a scale of 1 (best) to 5 (worst)

|  | Baseline | 0.0 g | 2.5 g | 5.0 g | 10.0 g | Washout |
|---|---|---|---|---|---|---|
| Bowel movement | 1.42 ± 0.55 | 1.57 ± 0.61 | 1.44 ± 0.55 | 1.39 ± 0.51 | 1.46 ± 0.61 | 1.42 ± 0.79 |
| Stool consistency | 1.56 ± 0.64 | 1.63 ± 0.68 | 1.54 ± 0.68 | 1.54 ± 0.73 | 1.57 ± 0.65 | 1.50 ± 0.84 |
| Discomfort | 1.42 ± 0.69 | 1.48 ± 0.60 | 1.56 ± 0.57 | 1.44 ± 0.65 | 1.52 ± 0.73 | 1.14 ± 0.38 |
| Flatulence | 1.52 ± 0.78 | 1.83 ± 0.75* | 1.85 ± 0.79* | 1.86 ± 0.75* | 2.07 ± 0.88* | 1.25 ± 0.55 |
| Abdominal pain | 1.17 ± 0.38 | 1.31 ± 0.49 | 1.33 ± 0.40 | 1.30 ± 0.50 | 1.30 ± 0.60 | 1.14 ± 0.41 |
| Bloating | 1.14 ± 0.33 | 1.39 ± 0.75 | 1.43 ± 0.47 | 1.30 ± 0.65 | 1.48 ± 0.90 | 1.08 ± 0.26 |

*Significant differences detected by ANOVA ($p < 0.05$) between the GOS and baseline and washout treatments.
Tukey's post-hoc test did not detect significant differences in pair-wise comparisons.

Example 9

Fecal Bacteria Counts

Cultural enumerations were performed for total anaerobic bacteria and for lactose-fermenting enterobacteria, enterococci, *Bifidobacterium*, and *Bacteroides*. *Lactobacilli* counts were very low (<106/g) throughout the entire duration of the study, even during treatment periods. When the data for each individual subject was analyzed, the results revealed that for some subjects, statistically significant differences in several of these groups were observed following consumption of GOS. When the results of all eighteen subjects were pooled together, no significant changes were detected for levels of *Bacteroides*, enterococci, or lactose fermenting enterobacteria. However, ANOVA revealed that GOS induced a modest, but statistically significant increase of bifidobacteria compared to the control treatment (Table 3). This bifidogenic effect occurred when subjects had consumed the 5 g dose of GOS, and a further increase in dose to 10 g of GOS was not significant when compared to the 5 g dose. In contrast, however, the 10 g dose did result in a significant increase in total anaerobes compared to the 2.5 g dose. In addition, the bacterial populations that was observed for all groups were similar during the baseline and washout periods.

The pHs of all of the fecal samples (288) were determined. All but two of the samples had pH values between 6.0 and 8.0, and there were no significant treatment differences in pH observed over the period of the study.

TABLE 3

Enumeration of bacterial groups through culturing
Log 10 CFU/g feces (mean ± SD)

| Bacterial Group | Baseline | 0.0 g | 2.5 g | 5.0 g | 10.0 g | Washout |
|---|---|---|---|---|---|---|
| Lactose fermenting Enterobacteria | 5.60 ± 1.14 | 5.68 ± 1.07 | 5.64 ± 0.86 | 5.18 ± 1.26 | 5.59 ± 0.85 | 5.78 ± 1.17 |
| Enterococci | 5.02 ± 0.99 | 5.02 ± 1.07 | 4.95 ± 0.99 | 4.67 ± 0.93 | 4.70 ± 0.90 | 5.13 ± 1.10 |
| Bifidobacteria | 9.32 ± 0.79 | 9.48 ± 0.73 | 9.60 ± 0.80 | 9.76 ± 0.48* | 9.83 ± 0.56*** | 9.42 ± 0.52 |
| Bacteroides | 9.56 ± 0.37 | 9.58 ± 0.37 | 9.59 ± 0.35 | 9.47 ± 0.32 | 9.53 ± 0.35 | 9.53 ± 0.33 |
| Total anaerobes | 10.19 ± 0.28 | 10.19 ± 0.20 | 10.11 ± 0.23 | 10.24 ± 0.15 | 10.35 ± 0.16**§§§ | 10.19 ± 0.21 |

Significantly difference to 0.0 g: *(p < 0.05), (p < 0.01),*(p < 0.001).
Significantly difference to 2.5 g: §§§(p < 0.001).

Example 10

Genus Specific qRT-PCR for Enumeration of Bifidobacteria

Figure 1:
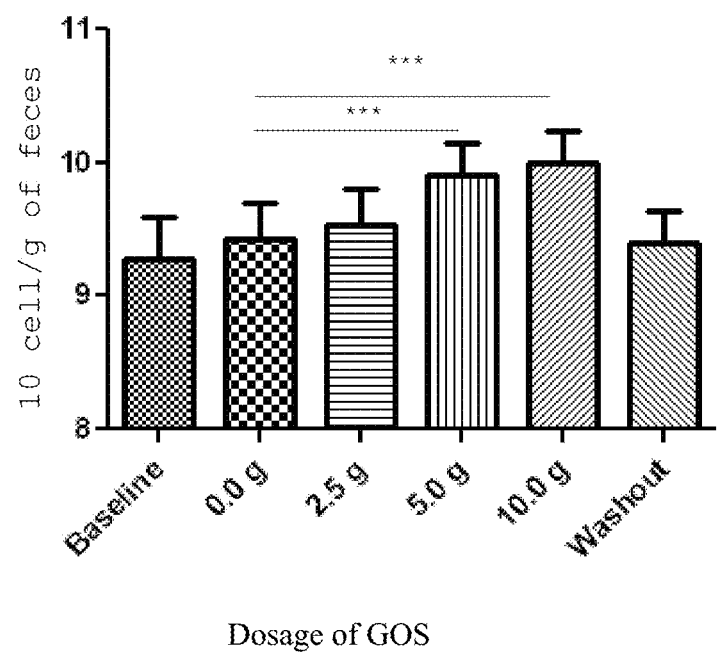
FIG. 1 is graphs showing the bifidogenic effect of GOS as determined by qRT-PCR for all eighteen subjects (A) and for the 9 responders (B). Significance (by ANOVA) is indicated at either $p<0.05$ (*) or $p<0.001$ (***).
Figure 1:
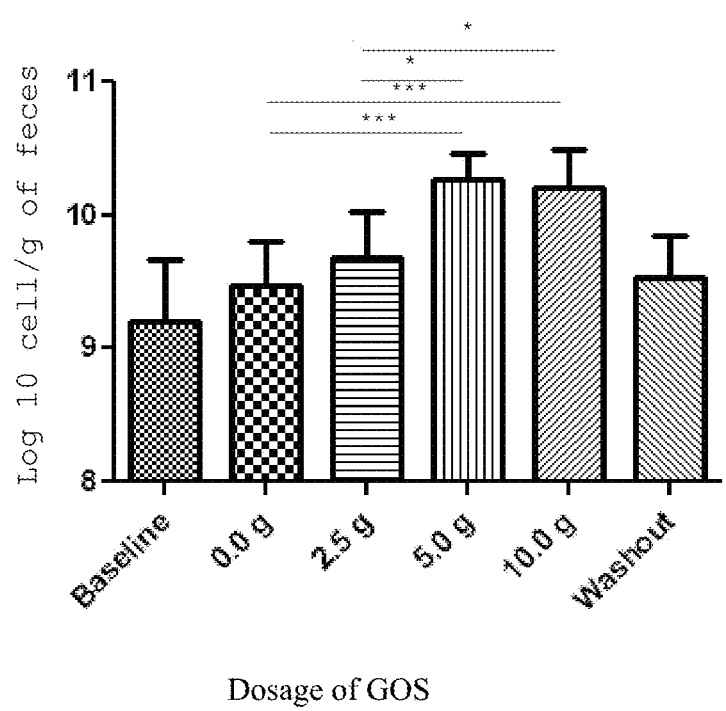

The culture analysis indicated that a bifidogenic effect occurred due to consumption of GOS, and that this effect was detectable at doses of 5 g and 10 g, with no significant differences between the two high doses. In order to confirm these findings without a potential cultivation bias, cell numbers of bifidobacteria in fecal samples were quantified by genus-specific qRT-PCR. As shown in FIG. 1A, the *Bifidobacterium* population in the eighteen subjects increased with the inclusion of chews containing different amounts of GOS. As before for cultural enumeration, this increase reached statistical significance when 5 g and 10 g of GOS were consumed (p<0.001). The analysis also showed major differences in the dose response relationships in individual subjects. In total, *Bifidobacterium* numbers were significantly increased by GOS consumption in nine of the eighteen subjects as analyzed by ANOVA. FIG. 1B shows the numbers of bifidobacteria in these nine "responders". This data showed an equivalent gradual increase of bifidobacteria with dose, with no significant differences between 5 and 10 g of GOS.

Figure 2:
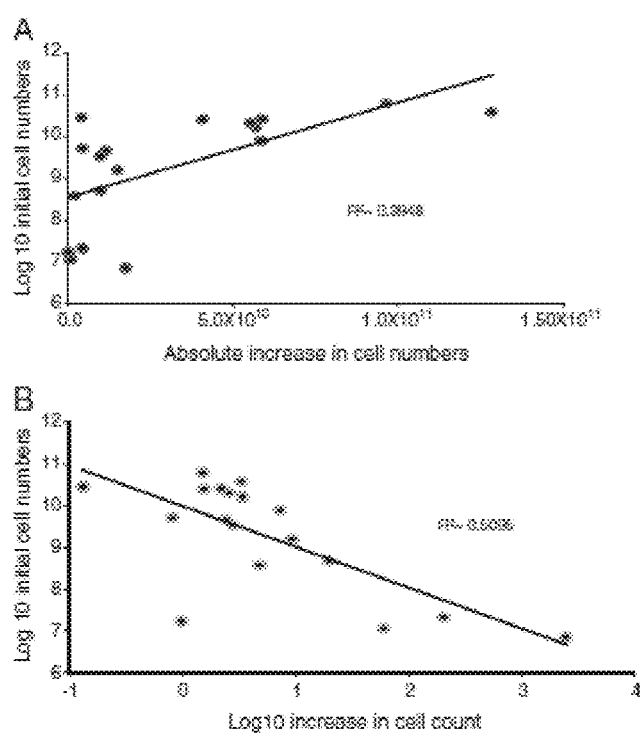
FIG. 2 is graphs showing the correlation of initial bifidobacteria levels (baseline) and the increase of bifidobacteria by GOS feeding (from the baseline to the average of the 5 and 10 g dose levels) as measured by absolute numbers (A) and by log increase (B).

To determine if the baseline *Bifidobacterium* population influenced the prebiotic effect, the initial bifidobacteria levels was compared between responders and non-responders. The Student's t test did not reveal any significant differences between these groups, indicating that initial number of bifidobacteria did not determine whether any specific individual was a responder or non-responder. In contrast, the baseline cell count of bifidobacteria in subjects was a major determinant for the bifidogenic effect when this effect was based on the difference in actual numbers from the baseline to the average of the 5 and 10 g treatments. As shown in FIG. 2A, initial levels of bifidobacteria directly correlated with the increase of bifidobacteria numbers. However, the bifidogenic effect, expressed as the "log increase", was inversely correlated with the initial bifidobacteria levels (FIG. 2B). In other words, subjects with low numbers of bifidobacteria had a higher potential for the prebiotic to induce a 100-1000 fold increase, while subjects that already possessed high levels of bifidobacteria were able to achieve an even higher increase in absolute numbers.

Example 11

Characterization of Total Fecal Bacterial Populations by PCR-DGGE

Figure 3:
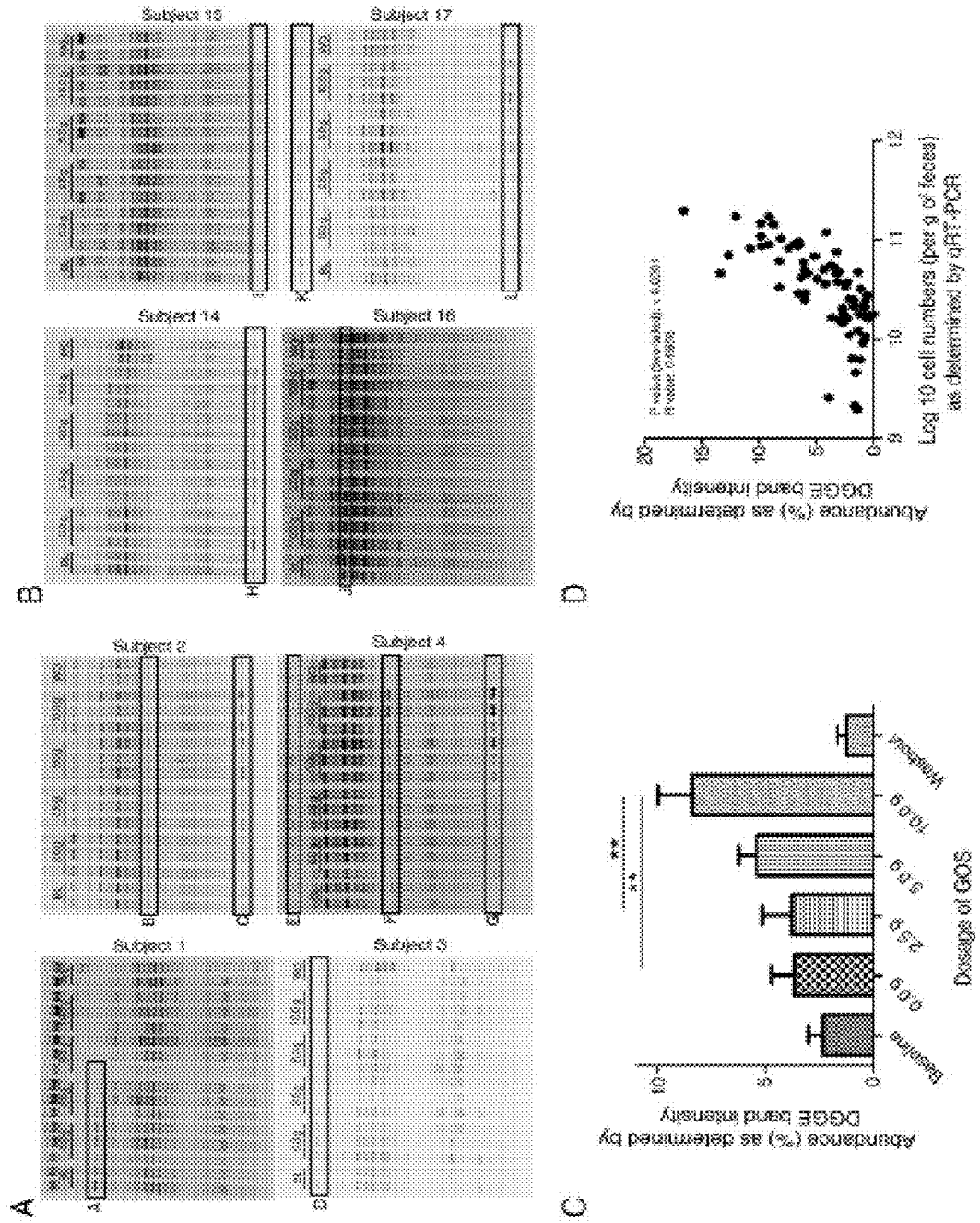
FIG. 3 shows DDGE analysis of fecal microbiota of subjects 1, 2, 3 and 4 (A) and 14, 15, 16 and 17 (B) by DGGE. Bands that were significantly affected by the GOS treatments are outlined. Abundance scores, as measured by DGGE band intensities, from bands C, G, H, I and L, as a function of GOS doses (C). Correlation of *Bifidobacterium adolescentis* band intensities from subjects 2, 4, 14, 15 and 17 for all time points to cell numbers, as measured by *Bifidobacterium* genus-specific qRT-PCR (D).

To obtain a broader assessment of the impact of GOS on the fecal microbiota, a universal PCR-DGGE approach was used to determine the dynamics of the community fingerprints. These analyses revealed a high level of stability among the gut microbiota in all of the subjects. The DGGE gels corresponding to the eight subjects with the most pronounced changes in staining intensities upon consumption of GOS are shown in FIG. 3. Quantification of DGGE band intensities was then performed using BioNumerics software, as previously reported (Martinez et al., 2009, supra), revealing several major effects (Table 4).

TABLE 4

Ratio of staining intensities of major bands as proportion of total fingerprint intensity (%).
Mean band intensity (±SD)

| Subject | DGGE fragment | Baseline | 0.0 g | 2.5 g | 5.0 g | 10.0 g | Washout |
|---|---|---|---|---|---|---|---|
| Increasing significance | | | | | | | |
| 2 | C | 3.68 ± 0.02 | 2.76 ± 0.009 | 4.87 ± 0.01 | 6.67 ± 0.03 | 11.89 ± 0.04**§ | 2.93 ± 0.02 |
| 4 | F | 3.13 ± 0.02 | 1.23 ± 0.001 | 3.83 ± 0.02 | 3.33 ± 0.005 | 6.96 ± 0.02** | 1.39 ± 0.002 |
|   | G | 1.46 ± 0.007 | 3.94 ± 0.02 | 2.70 ± 0.004 | 5.51 ± 0.01 | 9.75 ± 0.03*§§ | 1.21 ± 0.003 |
| 14 | H | 3.41 ± 0.16 | 6.40 ± 0.06 | 8.57 ± 0.02 | 7.41 ± 0.008 | 8.06 ± 0.02 | 0.69 ± 0.01 |
| 15 | I | 0.00 ± 0.00 | 0.00 ± 0.00 | 1.48 ± 0.002* | 2.53 ± 0.01** | 2.55 ± 0.002** | 0.00 ± 0.00 |
| 17 | L | 0.92 ± 0.002 | 1.73 ± 0.01 | 1.48 ± 0.01 | 5.15 ± 0.007 | 10.00 ± 0.03***§§§† | 0.60 ± 0.002 |
| Decreasing significance | | | | | | | |
| 1 | A | 11.91 ± 0.03 | 10.73 ± 0.03 | 2.79 ± 0.05* | 0.12 ± 0.001** | 0.19 ± 0.002** | 1.15 ± 0.01 |
| 2 | B | 5.07 ± 0.01 | 3.50 ± 0.01 | 3.17 ± 0.01 | 2.88 ± 0.003 | 1.03 ± 0.002 | 2.51 ± 0.01 |
| 3 | D | 6.51 ± 0.02 | 7.06 ± 0.03 | .42 ± 0.04 | 1.30 ± 0.02 | 0.001 ± 0.002 | 4.50 ± 0.004 |

TABLE 4-continued

Ratio of staining intensities of major bands as proportion of total fingerprint intensity (%).
Mean band intensity (±SD)

| Subject | DGGE fragment | Baseline | 0.0 g | 2.5 g | 5.0 g | 10.0 g | Washout |
|---|---|---|---|---|---|---|---|
| 4 | E | 1.88 ± 0.001 | 1.66 ± 0.005 | 3.35 ± 0.003 | 2.69 ± 0.02 | 0.35 ± 0.0009§ | 2.63 ± 0.02 |
| 16 | J | 9.74 ± 0.03 | 8.00 ± 0.03 | 7.15 ± 0.009 | 4.13 ± 06 | 4.10 ± 0.005 | 4.33 ± 0.004 |
| 17 | K | 8.70 ± 0.002 | 3.68 ± 0.04 | 6.79 ± 0.02 | 2.80 ± 0.02 | 0.63 ± 0.005 | 2.83 ± 0.004 |

Significantly different to 0.0 g: *($p < 0.05$), ($p < 0.01$), *($p < 0.001$).
Significantly different to 2.5 g: §($p < 0.05$), §§($p < 0.01$), §§§($p < 0.001$).
Significantly different to 5.0 g: †($p < 0.05$).
Subjects 3, 14, 2B, 16, 17K are included because they are approaching significance ($p < 0.05$) at 10 g compared to 0.0 g.

The most consistent alteration in band staining intensity resulting from consumption of GOS was a band at the bottom of the DGGE gels (labeled as C, G, H, I, and L), that was present in five subjects, 2, 4, 14, 15, and 17 (FIGS. 3A and 3B). Excision of the band and subsequent purification and DNA sequencing revealed that the band corresponded to *Bifidobacterium adolescentis* (Table 5). The staining intensity of this band clearly showed a dose dependent increase (Table 4), although differences were observed between subjects with respect to the effective dose (ranging from 2.5-10 g). However, when the band intensity values from these five subjects were averaged, the results revealed that a bifidogenic effect occurred only when the GOS dose reached 10 g (FIG. 3C).

*PLos ONE*, 5:e15046). Briefly, the V1-V3 region of the 16S rDNA gene was amplified by PCR from fecal DNA using primers adapted for the Roche-454 Titanium kit. A mixture (4:1) of the primers B-8FM: (5'-CCT ATC CCC TGT GTG CCT TGG CAG TCT CAG AGA GTT TGA TCM TGG CTC AG-3'; SEQ ID NO:5) and B-8FMBifido: (5'-CCT ATC CCC TGT GTG CCT TGG CAG TCT CAG AGG GTT CGA TTC TGG CTC AG-3'; SEQ ID NO:6), were used as the forward primers. The primer A518R: (5'-CCA TCT CAT CCC TGC GTG TCT CCG ACT CAG BBB BBB BBA TTA CCG CGG CTG CTG G-3'; SEQ ID NO:7) containing an 8-base barcode sequence was used as the reverse primer. Sequences were then assigned to their respective samples via the barcode. The

TABLE 5

| Subject | Band fragment | Closest related GenBank sequence (% similarity between DGGE fragment and GenBank sequence) |
|---|---|---|
| 1 | A | *Ruminococcus* uncultured bacterium; 29A-b4; DQ905715 (99%) |
| 2 | B | *Lachnospiraceae* uncultured bacterium; RL197_aah88b02; DQ794455 (100%) |
|   | C | *Bifidobacterium adolescentis*; E-981074T; nru-5; AF275882 (100%) |
| 3 | D | *Bacteroides* uncultured bacterium; NO48; AY916250 (100%) |
| 4 | E | *Bacteroides uniformis* (T); JCM 5828T; AB050110 (100%) |
|   | F | *Bacteroides dorei* (T); JCM 13471; 175; AB242142 (100%) |
|   | G | *Bifidobacterium adolescentis*; E-981074T; nur-5; AF275882 (99%) |
| 14 | H | *Bifidobacterium adolescentis*; E-981074T; nru-5; AF275882 (100%) |
| 15 | I | *Bifidobacterium adolescentis*; E-981074T; nru-5; AF275882 (100%) |
| 16 | J | *Ruminococcaceae* uncultured bacterium; RL185_11n85a07; DQ825073 (100%) |
| 17 | K | *Ruminococcus* uncultured bacterium; B086; DQ325583 (97%) |
|   | L | *Bifidobacterium adolescentis*; E-981074T; nru-5; AF275882 (100%) |

Collectively, the abundance of *B. adolescentis*, as determined by staining intensity, was remarkably quantitative and highly correlated to cell numbers as determined by qRT-PCR (FIG. 3D). Also, as shown in FIG. 3 and Table 4, the increase in *B. adolescentis* was reversible and returned to the baseline level within a week of wash out. Consumption of GOS also resulted in several other reversible alterations in the fecal microbiota; however, most of these alterations related to a decrease in staining intensity of bands that corresponded to different colonic microorganisms (Table 5).

Part B

Example 12

Analysis of the Fecal Microbiota by Pyrosequencing

Pyrosequencing of 16S rDNA tags was performed from fecal DNA as described previously (Martinez et al., 2010, 8FMBifido was used in combination with primer 8FM, as 16S DNA sequences within the genus *Bifidobacterium* are not well amplified by the latter primer (Martinez et al., 2009, supra).

Equal amounts of the PCR products were combined and gel purified and then sequenced with the 454/Roche A sequencing primer kit using a Roche Genome Sequencer GS-FLX. Sequences were binned according to barcodes, using the Ribosomal Database Project (RDP) Pyrosequencing Pipeline (pyro.cme.msu.edu/ on the World Wide Web) 'Initial Process' tool (Cole et al., 2009, *Nuc. Acids Res.*, 37:D141-5). Default parameters were established to remove sequences containing any ambiguous nucleotides, except for the minimum sequences length, which was set to 300 bp. BioEdit Software was used to trim the quality approved sequences to 450 bp before submission to the sequence analyses (see below).

Example 13

Sequence Analyses to Characterize Microbial Populations

Sequences obtained by pyrosequencing were analyzed using taxonomy-dependent and taxonomy-independent approaches. First, the Classifier tool of the RDP was applied (with a minimum bootstrap value of 80%) to obtain a taxonomic assignment of all sequences. The Classifier approach allowed a fast determination of the proportions of bacterial groups at different taxonomic levels (phylum to genus). Alternatively, the sequences were assigned to Operational Taxonomic Units (OTUs). Accordingly, all sequences from each subject were individually aligned using the RDP Aligner web tool, and then clustered using the RDP Complete Linkage Clustering web tool (with a maximum distance cutoff of 97%; Cole et al., 2009, supra). The OTU picking was performed on a per subject basis, as the entire data set from all of the subjects contained too many sequences for a quality alignment. OTUs that contained less than three sequences were excluded from the analyses. Using Statistical Analysis Software (SAS) to perform ANOVA, the OTUs that were significantly affected by the treatments in each subject were identified.

Representative sequences from each OTU whose abundance was significantly influenced by GOS were subjected to taxonomic classification using SeqMatch, an RDP web tool. From each statistically significant OTU identified, five random representative sequences were aligned to form consensus sequences using SeqMan Software (DNASTAR Lasergene). The consensus sequences were grouped and aligned according to phylum (Actinobacteria, Bacteroidetes, Firmicutes, Fusobacteria, Proteobacteria, and Verrucomicrobia), together with the most closely related type strains or entry in the NCBI database using Muscle 3.6 (Edgar, 2004, *Nuc. Acids Res.*, 32:1792-7). Phylogenetic trees were assembled by neighbor joining with 1,000 bootstrap replicates with MEGA 4.0 Software (Tamura et al., 2007, *Mol. Biol. Evol.*, 24:1596-9). Using visual analyses and a distance matrix, OTUs were assigned as sequence clusters with >97% identity, and consensus sequences were generated for each of the OTU sequence clusters, as described above.

Quantification of each OTU in each sample was performed by BLASTn analysis with a local database including all the quality controlled sequences generated by pyrosequencing. A BLASTn algorithm was used with a 97% cutoff (min. length 300 bp) to quantify each OTU within each sample. The OTUs that were closely related to *Bifidobacterium adolescentis* were quantified by BLASTn using a cutoff of 98% (min. length 300 bp) as clearly differentiated clusters could be identified that showed overlap with 97%. The quantification of OTUs in all subjects was then verified to ensure that individual sequences were not being assigned to different OTUs. In three occasions, OTUs that were initially identified as distinct had very high sequence similarities, and were thus merged together as single OTUs.

Example 14

Determination of Community Diversity

Two different methods, the generation of rarefaction curves and Shannon's index, were applied to determine the diversity of the fecal microbiota using 16S rDNA sequence data. The DNA sequences within each sample were aligned and clustered using RDP web tools Aligner and Complete Linkage Clustering. Individual cluster files corresponding to each fecal sample were used to construct Rarefaction curves and determine the Shannon's Index.

Example 15

Statistical Analysis

To identify differences in the composition of the fecal microbiota induced through dietary treatments (0.0 g, 2.5 g, 5.0 g, and 10.0 g GOS) in all eighteen subjects, one-way ANOVA tests with repeated measures were performed. Samples obtained during the baseline and washout periods were not included within the statistical analysis. Post hoc pair-wise comparisons were done using Tukey's method. P-values of <0.05 were considered significant unless otherwise stated.

Example 16

In Vitro Utilization of GOS by Bifidobacteria and Other Colonic Bacteria

A total of 39 strains of bifiodbacteria were screened for their ability to use GOS as a growth substrate. Included were 19 lab strains (from ATCC, commercial sources, and the Department of Food Science Culture Collection) and 20 isolates obtained from subjects as described above. Strains were grown anaerobically at 37° C. in MRS broth containing 2% GOS (GTC Nutrition, Golden Colo.). Because the latter material contains 92% GOS, with the balance as lactose, glucose, and galactose, control cultures were prepared that contained an equivalent amount of these sugars (i.e., 0.16% final concentration). In addition, twenty-two anaerobic bacteria that were mainly of intestinal origin were also screened for their ability to use GOS as a growth substrate. All bacteria were obtained from the USDA ARS Culture Collection (Peoria, Ill.) and included strains of *Bacteroides thetaiotamicron, Bacteroides distasonis, Bacteroides fragilis, Bacteroides uniformis, Bacteroides ovatus, Clostridium butyricum, Clostridium histolyticum, Clostridium bifermentans, Clostridium difficile, Clostridium innocuum, Clostridium paraputrificum, Clostridium perfringens, Clostridium ramosum, Clostridium rumen, Clostridium sporogenes, Enterococcus faecalis, Enterococcus faecium, Enterobacter aerogenes*, and *Streptococcus salivarius*. Bacteria were initially propagated in Brain Heart Infusion (BHI) or Reinforced Clostridial Agar (RCA). To assess growth on GOS, cells were transferred (2%) into a basal medium [5 g/L Peptone No 3 (BD), 5.0 g/L Casitone (BD), 0.5 g/L L-Cysteine (Sigma), 40 mL Salt Solution, 10 mL Hemin (Sigma), 900 µL Vitamin K3 (Sigma), and 1 g/L Yeast Extract (BD)] containing 1% GOS (GTC Nutrition, Golden, Colo.). Control cultures containing 0.08% mono- and disaccharides were prepared as above.

All cultures were incubated at 37° C. in an anaerobic chamber (Forma Scientific, Marietta, Ohio) containing an atmosphere of 85% nitrogen, 10% hydrogen, and 5% carbon dioxide and assessed for growth by optical density measurement at 600 nm in a Beckman Model 640 spectrophotometer. Each experiment was done in triplicate and the average optical densities were determined.

Example 17

The Effect of GOS on the Fecal Microbial Communities

A total of 288 fecal samples were included in this study. Pyrosequencing resulted in a total of 2.3 million sequences.

After quality control analysis (see Methods), an average of 8,200 sequences per sample was obtained. The mean sequence length was approximately 450 bp. An average of 2,022 OTUs was identified per subject. To assess the effect of GOS on the bacterial diversity in fecal samples, rarefaction curves for all eighteen subjects were generated, and Shannon's diversity indices were calculated. This analysis revealed that consumption of GOS did not alter bacterial diversity of the fecal samples ($p<0.0713$).

The overall composition of the gut microbiota in the 18 individuals included in this study is in general agreement with that of previous studies (Turnbaugh et al., 2009, Nature, 457: 480-4). During the baseline period (no dietary modulation), the microbiota was dominated by two phyla, Firmicutes (64%) and Bacteroidetes (28%). Other phyla detected included Actinobacteria (3%), Verrucomicrobia (1%), and Proteobacteria (1%). Approximately 3% of the sequences remained unclassified. At the family level, the predominant groups were the Lachnospiraceae (31%), Ruminococcaceae (18%), Bacteroidaceae (12%), and Bifidobacteriaceae (2%). The most common genera included *Bacteroides* (12.2%), *Fecalibacterium* (7.7%), *Blautia* (7.4%), *Ruminococcus* (3.7%), *Roseburia* (2.2%), *Bifidobacterium* (1.5%), and *Dorea* (1.3%).

Sequence proportions determined by pyrosequencing were used to determine the effect of GOS on the composition of the gastrointestinal microbiota. The groups that were significantly affected are shown in Table 6, according to phylum, family, genus (by RDP Classifier), and OTUs. The control treatment (0.0 g GOS in confections) had no effect on the fecal microbiota, as the microbial populations during this period were not significantly different from those during the baseline and washout periods (although slight increases in the family Bacteroidaceae and the genus *Bacteroides* were detected). In addition, no significant changes in the fecal microbiota were detected for a dose of 2.5 g GOS. In contrast, consumption of 5.0 g GOS led to several significant changes. There were significant increases ($p<0.05$) in the family Bifidobacteriaceae and the genus *Bifidobacterium* compared to the control dose. At the species level, the abundance of only one OTU, corresponding to the species, *Fecalibacterium prausnitzii*, increased significantly at this dose. In contrast, significant decreases in abundance were observed at both the family and genus levels for Bacteroidaceae ($p<0.01$) and *Bacteroides* ($p<0.01$), respectively, at the 5.0 g dose compared to the control.

TABLE 6

Abundance of bacterial taxa affected by GOS consumption in fecal samples of eighteen human subjects as determined by pyrosequencing of 16S rRNA tags.
Proportion of bacterial taxa expressed in percentage (Mean ± SD)

| | Baseline[1] | 0.0 g[2] | 2.5 g[2] | 5.0 g[2] | 10.0 g[2] | Washout[1] | P value[3] |
|---|---|---|---|---|---|---|---|
| Phylum | | | | | | | |
| Actinobaceria | 2.52 ± 2.34 | 2.58 ± 3.59 | 3.69 ± 4.33 | 5.39 ± 6.11 | 7.19 ± 8.88 | 2.09 ± 2.51 | <0.0001 |
| Family | | | | | | | |
| Bfidobacteriaceae | 1.56 ± 2.14 | 1.69 ± 2.65 | 2.50 ± 3.43 | 4.27 ± 5.18 | 6.14 ± 7.08***§§ | 1.24 ± 2.10 | <0.0001 |
| Bacteroidaceae | 12.22 ± 7.43 | 15.03 ± 10.66 | 13.29 ± 9.24 | 11.20 ± 9.11** | 11.66 ± 9.22** | 13.69 ± 8.27 | 0.0030 |
| Genus | | | | | | | |
| *Bifidobacterium* | 1.28 ± 1.81 | 1.40 ± 2.20 | 2.13 ± 2.99 | 3.61 ± 4.46 | 5.20 ± 6.18***§§ | 1.05 ± 1.82 | 0.0002 |
| *Bacteroides* | 12.22 ± 7.43 | 15.03 ± 10.66 | 13.29 ± 9.24 | 11.20 ± 9.11** | 11.66 ± 9.22** | 13.69 ± 8.27 | <0.0001 |
| Species (OTUs) | | | | | | | |
| *bifidobacterium adolscentis* | 0.37 ± 0.56 | 0.34 ± 0.89 | 0.46 ± 0.86 | 0.85 ± 1.09 | 1.03 ± 1.55* | 0.21 ± 0.48 | 0.010 |
| *Bifiobacterium ssp I* | 0.15 ± 0.36 | 0.18 ± 0.33 | 0.25 ± 0.55 | 0.52 ± 1.13 | 0.77 ± 1.41*§ | 0.12 ± 0.25 | <0.0001 |
| *Bifidobacterium spp II* | 0.46 ± 0.94 | 0.60 ± 1.53 | 0.76 ± 1.72 | 1.41 ± 2.38 | 2.00 ± 3.45*§ | 0.22 ± 0.45 | <0.0001 |
| *Bifidobacterium spp III* | 0.62 ± 1.21 | 0.78 ± 2.19 | 0.98 ± 2.02 | 1.82 ± 3.30 | 2.50 ± 4.55*§ | 0.40 ± 0.92 | 0.0088 |
| *Bifidobacterium longum* | 0.09 ± 0.23 | 0.09 ± 0.23 | 0.12 ± 0.32 | 0.22 ± 0.50 | 0.33 ± 0.85* | 0.15 ± 0.38 | 0.0232 |
| *Bifidobacterium cantenulatum* | 0.15 ± 0.34 | 0.27 ± 0.88 | 0.56 ± 1.38 | 0.51 ± 1.16 | 0.91 ± 2.08** | 0.28 ± 0.78 | 0.0105 |
| *Faecalibacterium prausnitzii* | 3.52 ± 2.71 | 3.21 ± 2.26 | 3.71 ± 2.67 | 4.37 ± 3.67 | 3.16 ± 1.82† | 3.42 ± 2.28 | <0.0001 |
| *Coprococcus comes* | 2.90 ± 2.04 | 2.40 ± 1.75 | 2.12 ± 1.24 | 1.99 ± 1.55 | 1.78 ± 1.11* | 2.15 ± 1.30 | <0.0001 |

[1] Bacteria populations are averages of the two time points of the baseline period and the two time points of the washout 2 period.
[2] Bacteria populations are averages of all three time points of the feeding period.
[3] Bacterial populations during the dietary treatments were compared to each other with repeated measures ANOVA and Tukey's post hoc test.
Significantly different to 0.00 g: *($p < 0.05$), ($p < 0.01$), *($p < 0.001$).
Significantly different to 2.5 g: §($p < 0.05$), §§($p < 0.01$).
Significantly different to 5.0 g: †($p < 0.05$).

At the 10.0 g GOS dose, additional differences in the proportions of several phyla (using taxonomy-based analysis) were observed (Table 6). There was a significant increase in Actinobacteria compared to the control ($p<0.001$), as well as compared to the 2.5 g dose ($p<0.05$). This change was associated with an increase both in the family Bifidobacteriaceae, the genus *Bifidobacterium*, and several OTUs related to *Bifidobacterium* species. Although there were not significant differences between the 5 gram and 10 gram dose in Bifidobacteriaceae, the genus *Bifidobacterium*, and *Bifidobacterium* species, the amount of bifidobacteria at 10 gram GOS was consistently higher than at 5 gram. In addition, bifidobacteria were significantly increased at 10 gram GOS when compared to the 2.5 gram dose (Table 6). Collectively, the abundances of bifidobacteria determined by pyrosequencing were highly correlated (r=0.7629, p<0.0001) with the cell counts obtained by qRT-PCR as described above. This supports previous findings that show that the pyrosequencing approach allows a quantitative determination of bifidobacteria in human fecal samples.

Figure 7B:
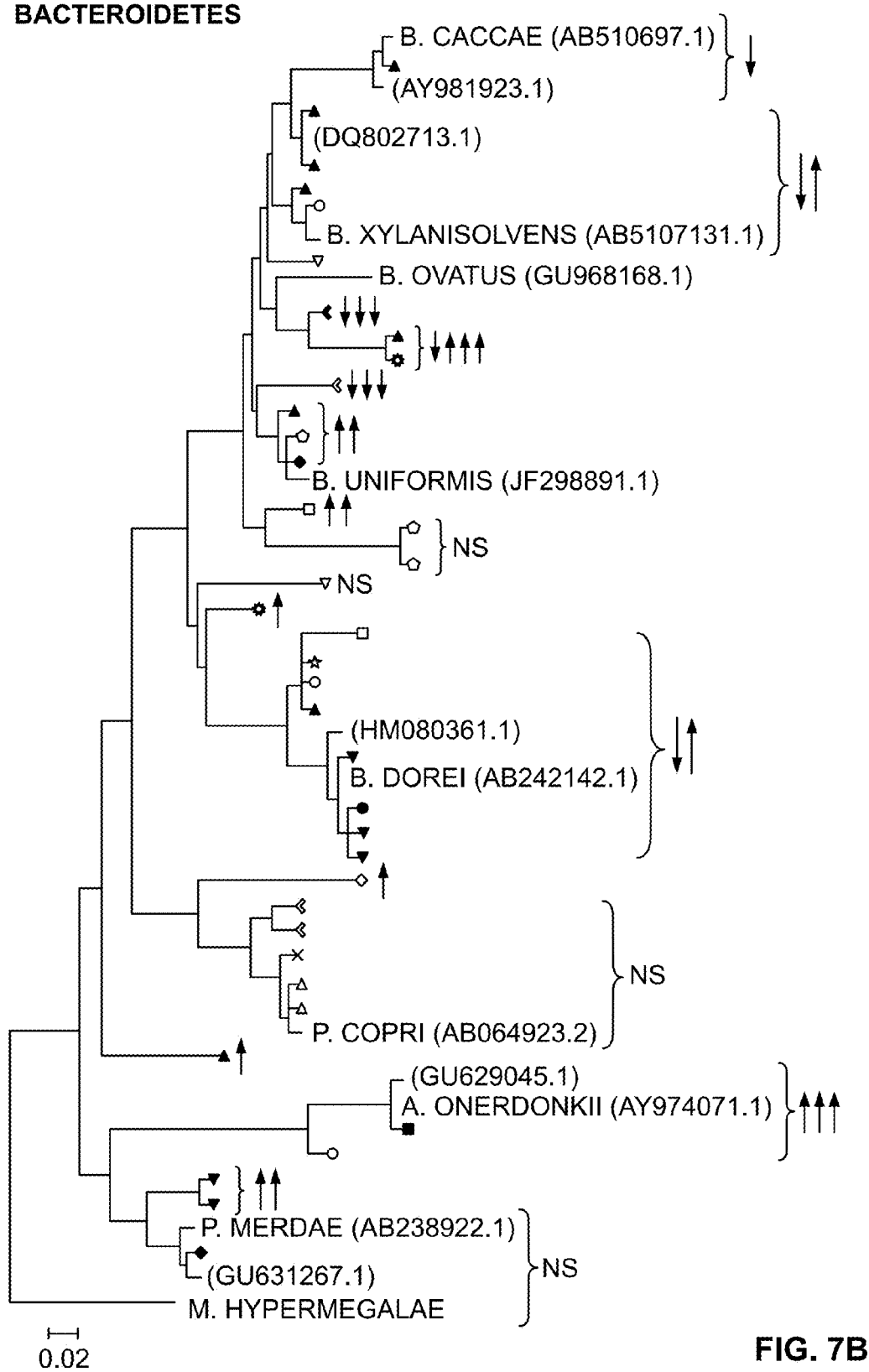

There were few bacterial taxa other than bifidobacteria that were influenced by GOS, based on a taxonomy-based analysis (Table 6). Statistically significant decreases were observed only within the family Bacteroidaceae (p<0.05) and the genus *Bacteroides* (p<0.05) when compared to the control dose of GOS. In contrast, the OTU-based approach identified two additional taxa, *Coprococcus comes* and *F. prausnitzii*, whose abundances differed significantly at 5 and 10 g doses. However, no trend was apparent from these results (Table 6). Although few taxa were identified that significantly decreased with the administration of GOS when all 18 subjects were assessed collectively, our analysis nonetheless showed that different bacterial lineages were decreased in individual subjects. As shown in FIG. 7, the changes were detected in a small number of subjects and occurred primarily within taxonomically diverse members within the phyla Firmicutes (FIG. 7A) and Bacteroidetes (FIG. 7B). Most of these taxa were reduced by GOS, but no consistent pattern was detected among subjects. Thus, it appears that although GOS induces a rather selective increase of different lineages of bifidobacteria, GOS does not result in a consistent increase of another bacterial group or a significant decrease of particular bacterial groups.

Example 18

GOS Enhances Different Lineages of Bifidobacteria

A BLASTn analysis revealed that eight OTUs had statistically significant changes in abundance at the 10 g GOS dose, six of which were assigned to the genus *Bifidobacterium*. Three of the OTUs showed a high similarity (>97%) to described *Bifidobacterium* species, *B. adolescentis*, *B. longum*, and *B. catenulatum* (Table 6, FIG. 4A). The other OTUs (*Bifidobacterium* spp I, II, and III) showed lower sequence similarities (91-96%) to known *Bifidobacterium* species, and the phylogenetic analysis shown in FIG. 4A revealed that these OTUs belonged to lineages clearly distinct from known type strains. Interestingly, two of these OTUs (*Bifidobacterium* spp II and *Bifidobacterium* spp III), showed the numerically highest response to GOS (Table 6, FIG. 4A).

Example 19

The Population Shifts Induced by GOS Vary Among Individuals

Although the consumption of GOS at the higher doses resulted in compositional shifts within subjects on a collective basis (FIG. 4B), closer examination of samples from individual subjects revealed that the effect of GOS on the intestinal composition of participants was subject to considerable variation among individuals (FIG. 5). Indeed, the data showed that there were some individuals that were essentially unaffected by GOS consumption, whereas other experienced significant changes. The most substantial alteration was the increase in the Actinobacteria (at the phylum, family, genus, and species levels) which was observed in sixteen of the eighteen subjects after 5.0 g and seventeen of the subjects after 10.0 g of GOS. At the genus level, in particular, substantial increases were observed in the abundances of *Bifidobacterium*, which increased approximately ten-fold (from 1-4% up to 18-33%) in four subjects (subjects 2, 4, 11, and 17), and five-fold in seven additional subjects (subjects 1, 9, 10, 15, 18). Several culturable isolates (NEGOS 1-3) were obtained from these subjects and were found to associate within the distinct *Bifidobacterium* spp. II lineage (FIG. 4A), indicating that this GOS responding linage contains bacteria that can be cultured. There was a very consistent reduction in the Bacteroidetes (at the family, genus, and species levels), which occurred within all of the subjects at some point after 5.0 g of GOS was consumed (FIG. 5). At the genus level, there was a decrease in the abundance of *Bacteroides* in 17 subjects after the 5.0 g GOS dose (all except subject 4), with 14 of those subjects having a further decrease after consumption of 10.0 g of GOS.

Example 20

Temporal Dynamics of Microbial Populations in Response to GOS

Analyses of the community profiles provided insight into how GOS influenced the population dynamics over the entire 16 week study period. All of the changes induced by GOS were reversible within one week, and no differences (Student's t-test, p>0.05) could be detected in the proportions of the bacterial groups between the first washout sample and the baseline sample (FIG. 6). The temporal patterns of the three main phyla (Actinobacteria, Bacteroidetes, and Firmicutes) and two of the selected genera (*Bifidobacterium* and *Bacteroides*) for five representative subjects showed that these groups were stable in their temporal response to GOS. For example, levels of Actinobacteria, Bacteroidetes, and Firmicutes were remarkably stable in fecal samples at the baseline and washout periods, and their populations returned to the baseline level within one to two weeks after GOS consumption was stopped. The same observations were also made at the genus level for *Bifidobacterium* and *Bacteroides*.

Example 21

In Vitro Growth of Gastrointestinal Microbiota Cultures on the Prebiotic GOS

As shown above, GOS induces alterations to the human fecal microbiota that are remarkably specific for bifidobacteria. However, GOS utilization was observed to be a strain-specific phenotype, at least based on in vitro growth studies (Table 7). It was also considered whether or not the ability to utilize GOS as a growth substrate was restricted to bifidobacteria and absent in other colonic bacteria. Therefore, the ability of twenty-two strains of bacteria that are associated with the human intestinal tract to utilize GOS was tested. This was performed by comparing growth in media containing GOS with growth in basal medium (i.e., without an additional source of carbohydrate). This experiment revealed that 6 of the 11 *Clostridium* strains could utilize GOS (FIG. 8), as indicated by higher final cell densities compared to growth without carbohydrates. In addition, three of the six strains of *Bacteroides* were also significantly enriched when GOS was present. Significant growth on GOS was not observed, however, for strains of the genera *Enterococcus, Enterobacter*, or *Streptococcus* used in this study.

TABLE 7

| Species (total number) | Number positives (%) | Number negative (%) |
|---|---|---|
| B. adolescentis (10) | 6 (60) | 4 (40) |
| B. bifidum (6) | 5 (84) | 1 (16) |
| B. breve (2) | 1 (50) | 1 (50) |
| B. animalis subsp. Lactis. (1) | 1 (100) | 0 |
| B. longum subsp. Infantis (2) | 2 (100) | 0 |
| B longum subsp longum (9) | 6 (67) | 3 (33) |
| B. pseudocatenulatum (3) | 2 (67) | 1 (33) |
| Other Bifidobacterium spp. (6) | 3 (50) | 3 (50) |
| Total (39) | 26 (67) | 13 (33) |

Part C

Example 22

Summary of Part A and Part B

Isolates of the genus Bifidobacterium were obtained from responders while the subjects were consuming 10 grams of GOS. As shown in FIGS. 9A and 9B, 10 grams of GOS led to an increase in the proportion of bifidobacteria in the fecal samples of one subject from around 3% to around 20%, and an increase of the Bifidobacterium spp. II lineage from around 3% to 10%, as determined by 16S rRNA tag pyrosequencing. Absolute quantification using qRT-PCR confirmed that bifidobacteria numbers increased in the fecal samples of this subject through the addition of GOS (FIG. 9C). From this subject, three bacterial isolates were obtained from selective agar plates (Rogosa SL Agar) during the consumption of 10 gram GOS. All three isolates belong to the Bifidobacterium spp. II lineage, which showed a marked increase through GOS (FIG. 9B) and two of these isolates represented the same strain based on molecular typing. One isolate, BD1 (97% homology to the type strain of Bifidobacterium adolescentis when the entire 16S rRNA gene was analyzed), was tested for its ability to ferment GOS. As expected for a lineage that became enriched in vivo through the administration GOS, strain BD1 showed a remarkable ability to utilize GOS, growing as well as on lactose (FIG. 9D).

Example 23

Research Design and Protocol

The study is organized as a randomized, placebo-controlled, parallel-arm clinical trial conducted at Rush University Medical Center (RUMC) under the supervision of Dr. Heather Rasmussen. The trial includes six, 3-week treatments using obese (BMI=30.0-40.0 kg/m$^2$) subjects who are healthy (but the study allows subjects with elevated liver enzymes due to fatty liver and metabolic syndrome). Three-week treatment length was selected to allow sufficient epithelial cell turnover. A total of 180 subjects are recruited and randomly assigned to six groups (n/group=30) as follows:
Group 1: Placebo (daily dose of 5 gram lactose)
Group 2: Probiotic 1: 10$^9$ cells of B. adolescentis BD1
Group 3: Probiotic 2: 10$^9$ cells of B. animalis subsp. lactis BB-12.
Group 4: Synbiotic 1: InVivoSyn (5 gram GOS plus 10$^9$ cells of B. adolescentis BD1)
Group 5: Synbiotic 2: 5 gram GOS plus 10$^9$ cells of B. animalis subsp. lactis BB-12
Group 6: Prebiotic (5 gram GOS)

Three visits are required from each subject. At Visit 1, potential subjects are screened for eligibility and are provided with a 3-day diet record, all supplies for stool and urine collection (stool kit, urine collection containers, sugar cocktail, and aspirin) and instructions for specimen handling and for completing these tasks before the next visit. Each subject collects the stool before taking the sugar cocktail to avoid potential effects of sugar cocktail on SCFA and microbiota composition. Details of the stool and urine collection are shown in FIG. 10.

In brief, the sugar cocktail is taken at 6 or 7 AM after an overnight fast. Subjects collect all urine for 24 hours (first 12 hour in one jar and second 12 hour in second jar). The subject repeats the sugar cocktail ingestion and urine collection 12 hours after taking 2.6 gram of aspirin to induce intestinal permeability. The subject is instructed to store the urine and stool samples in Styrofoam coolers with freezer packs until delivery to the hospital (not >than 3 days after collection). At Visit 2, the study subject provides urine from the aspirin challenge and the completed food record; subjects also have their blood drawn for CMP and endotoxin measurements (after 8 hour fasting) at this visit. Endotoxin is only assessed after aspirin challenge since previous research showed that aspirin challenge was necessary to induce hyperpermeability in susceptible obese individuals. Additional serum and plasma is collected and stored in −80 freezer for future study (measurement of lipid profile and insulin to calculate HOMA index for metabolic syndrome and cytokines, CRP). Urine is stored for future 12-hour cortisol measurements. Subjects are provided with one of the six treatments (as determined by randomization, see below), supplies for stool and urine collection identical to baseline. Subjects consume their randomly assigned supplement daily for three weeks as instructed. At the end of three weeks (within week 3), subjects return to the clinic to provide stool, urine as previously described for week 0-1. At the final visit after 3 weeks of supplementation, the subjects provide the remaining urine sample, and 3-day food records. Subjects provide fasting blood for endotoxemia and CMP measurements and stored serum and complete questionnaires regarding adverse events including a questionnaire that rates bowel movement, stool consistency, discomfort, flatulence, abdominal pain, and bloating on a scale from 1 (best) to 5 (worst). Weight, height, waist circumference, and blood pressure is measured, and BMI is calculated at each visit. Blood pressure is measured using an automated cuff with the average of three assessments used for statistical comparisons. In addition, stress is monitored at baseline and treatment end using the validated Perceived Stress Questionnaire as stress alone can increase permeability. The necessary protocol approvals are obtained from RUMC and UNL's Institutional Review Boards (IRB) before initiation of the study, and subjects provide written informed consent before any study procedures are performed.

Example 24

Subject Compliance and Education

A training session is held to explain the protocol to the subjects, how to consume the dietary items, the importance of compliance, and the need for honesty if adherence to the dietary treatment is not met. Subjects are provided with a detailed explanation of the required commitment, and they are encouraged to indicate to the clinical coordinator any diversion from the dietary treatment and to return any products that were not consumed. Regular interaction with the subjects by weekly phone calls is also encourage compliance. Missing data is handled with the Last Observation Carried Forward method.

Examples 25

Subjects

Obese subjects (30.0-40.0 kg/m$^2$) are used for this study because: (1) over ⅓ of the population is obese, and (2) these individuals are predispositioned to hyperpermeability. An equal number of both genders (50% each) are enrolled. It is an aim to include approximately 40% minorities (30% African American, 10% Hispanic or other minorities) in this study. This enrollment of minorities is especially important because obesity is especially preponderant in these minority groups.

Inclusion criteria include healthy subjects 18-60 years with a BMI of 30.0-40.0 kg/m$^2$. Exclusion criteria include: (1) prior intestinal resection, (2) patient history of GI diseases except for hiatal hernia, GERD, hemorrhoids, (3) severe renal disease defined by creatinine more than twice normal, (4) markedly abnormal liver function defined by ALT/AST over 4 times normal levels or elevated bilirubin (5) antibiotic use within the last 12 weeks prior to enrollment, (6) lean or overweight (BMI<30 kg/m$^2$), (7) intolerant to aspirin, (8) regular use of aspirin, (9) excessive alcohol intake (>2 drinks for men or 1 drink for women daily), (10) presence of chronic metabolic disease (cardiovascular disease, insulin requiring diabetes or uncontrolled diabetes, cancer, (11) a plan to have a major change in dietary habit during the following 6 months, (12) consumption of probiotics, prebiotics or synbiotics without an appropriate 4 week washout period, (13) lactose intolerance or malabsorption; (14) subjects younger than 18 or older than 60, and/or (15) unwillingness to consent to the study.

Examples 26

Randomization/Stratification/Blinding

The study participants are randomized (concealed, block of 4) to one of the six treatment groups on their second visit based on a computer-generated randomization. Randomization is stratified for gender and race to ensure equal numbers of males and females and racial groups in each of the six treatments. The randomization is concealed and remains blinded until completion of the study. The statistician also is blinded, with the exception of having access to a subject's identification numbers that belong to the six randomized groups for analysis purposes. The study participants also are blinded to the group assignment. The number of sachets to be taken daily and the shape of sachets is identical in all six groups. The sachets are opaque and their contents are not visible. Expectancy and credibility are measured in both pre- and post-treatment to determine the role that these factors play in outcomes, and to confirm that the subjects were blinded.

Examples 27

Power and Sample Size

Analysis showed that 40 subjects are needed for each group to reach statistical significance (power>0.85; p<0.05).

Examples 28

Dietary Treatments

The two organisms that are used in this feeding study are *B. adolescentis* BD1 and *B. animalis* BB-12. The latter is commercially available from Chrs. Hansen as a high cell density powder. Strain BD1 is produced from a contract manufacturer (Danwell Technology, Garden Grove, Calif.). Probiotic mixtures subsequently are portioned into "sachets" in the Food Processing Product Development Lab (UNL). Each sachet contains 1 g of cell powder containing 10$^9$ CFU/g. In addition, 5.5 grams of lactose also is added as a carrier/control (see below) for a total dose of 6.5 g. The sachet material is impermeable to oxygen and moisture. The prebiotic, GOS, is obtained from Corn Products International (sold under the trade name, Purimune). This high purity GOS (>91%) contains less than 8% lactose. It was previously established that a dose of 5 g per day of this GOS was sufficient to induce a bifidodogenic response and that a dose as high as 10 g/day did not cause side-effects. The GOS is packaged in sachets containing 5.5 g of Purimune (delivering 5 g of GOS) and an additional 1.0 g of lactose, for a total dose of 6.5 g. Synbiotics contain 5.5 g of Purimune and 1.0 g of probiotic, either *Bifidobacterium adolescentis* BD1 or *Bifidobacterium animalis* BB-12, for a total dose of 6.5 g. Placebo samples contain 6.5 g of lactose. Subjects are provided with enough samples for the entire length of the study. Subjects are instructed to consume each dose in a daily basis, either mixed with food or liquid. The subjects are instructed to store samples in a cool (<25° C.) environment.

Example 29

Analysis of Composition Fecal Microbiota

Frozen fecal samples are thawed and diluted in Phosphate Buffered Saline (PBS) in a 1:10 ratio. DNA is isolated and gut microbiota composition is analyzed by pyrosequencing of 16S rRNA tags. Briefly, total microbial DNA is isolated from the fecal samples using a procedure that employs both enzymatic and mechanical cell disruption. The V1-V3 region of the 16S rRNA gene of the bacteria present in the fecal sample is amplified by PCR from fecal microbial DNA by using a combination of universal PCR primers that target the majority of bacteria. The amplicons from each reaction is mixed in equal amounts based on concentration and is subjected to sequencing using a Roche Genome Sequencer GS-FLX using the Titanium platform. This method results in around 300,000-500,000 sequence reads per half-run after quality control, and allows for a detailed characterization of the gut microbiota via bioinformatic pipelines.

Example 30

Determination of Absolute Cell Numbers of Probiotic Strains and Total Bifidobacteria in Fecal Samples Quantitative real-time PCR (qRT-PCR) is used to quantify strains BD1 and BB-12 in human fecal samples. DNA is isolated from human fecal samples and qRT-PCR is performed to determine absolute cell numbers of the two strains using qPCR with strain specific primers. The primers are targeted towards strain specific sequences in the pan-genome of the species. The genome of *B. animalis* subsp. *lactis* BB-12 is available, and the genomic sequence of *B. adolescentis*

BD1 is currently being obtained. Total numbers of bifidobacteria are determined by qRT-PCR. Absolute quantification by qRT-PCR is performed in a Mastercycler realplex real-time PCR system using standard curves generated with known cell numbers of the two *Bifidobacterium* strains.

Example 31

Short-Chain Fatty Acid Analysis and Energy Content

Short-chain fatty acids (SCFA), including acetate, propionate, and butyrate, are identified by GC in the Analytical Chemistry Lab in the Department of Food Science and Technology at UNL.

Example 32

Determination of Metabolic Activity of Probiotic Strains in Human Fecal Samples

To determine if GOS increases the metabolic activity of the *Bifidobacterium* strains in the human gastrointestinal tract, both rRNA and rDNA templates in human fecal samples is quantified using species specific primers. This determination is based on the premise that metabolic activity in bacteria is roughly proportional to the growth rate of the bacteria. While DNA-based analytical procedures provide a phylogenetic picture of the community, they do not reflect metabolic activity. The higher the ratio between rRNA to rDNA templates in fecal samples, the more metabolically active is the organism. Total RNA (and especially ribosomal RNA) is isolated from fecal samples. cDNA is prepared from DNAse treated RNA. Template amounts are determined using qRT-PCR with specific primers that target the 23S rRNA gene. The primers are based on comparisons of 23 rRNA gene sequences from *Bifidobacterium adolescentis* strains and sequences that are available in database. This 23S rRNA gene sequence is variable in *B. adolescentis*, showing around 2% difference between the strains ATCC 15703 and L2-32, allowing the development of primers that are, at least to some degree, strain specific.

Example 33

Intestinal Permeability Measurement

One way to assess intestinal permeability is by administration of oral sugars and analysis of subsequent sugar excretion in collected urine. Passageways ("pores") formed by tight junctions between GI epithelial cells range in size from 4-60 Å and differentially allow the passage of molecules. Small molecules such as mannitol traverse pores of all sizes, while larger molecules, such as lactulose, only traverse the larger pores. Sucrose is rapidly degraded after leaving the stomach, so increased sucrose excretion reflects gastric permeability and sucralose is absorbed through large pores in the small and large intestine. Since these sugars are not metabolized significantly, excretion into the urine reflects intestinal permeability. Following ingestion of a standard sugar load, increased urinary sucrose, lactulose/mannitol ratio and sucralose reflects gastroduodenal, small intestinal and total gut (small bowel and large bowel) hyperpermeability, respectively. Increased sucralose excretion in the face of normal lactulose/mannitol ratio might reflect increased large intestinal permeability. The rationale for using urinary sucralose as a reliable marker of total gut permeability is that not only sucralose is relatively uniformly absorbed in both small and large intestine it is also available in the lumen of colon for absorption because, unlike lactulose and mannitol, it cannot be metabolized and consumed by colonic bacteria.

Subjects fast overnight and subsequently ingest a sugar mixture containing 2 grams mannitol, 7.5 grams lactulose, 40 mg sucrose and 1 gram sucralose in the morning, then collect 2 sequential 12-hour urinations (the first 12 hours for measurement of lactulose and mannitol, and 24 hours for sucralose). Urine is analyzed for sugar content using gas chromatography (GC) techniques. Measurement of urinary sugars using GC is used to calculate intestinal permeability and is expressed as percent oral dose excreted in the urine. A method is used that involves conversion of the relevant sugars to their alditol acetate form.

While obese individuals are at an increased risk of hyperpermeability, increases in permeability may not be observed unless challenged by other factors such as aspirin or alcohol. In order to induce hyperpermeability, subjects participate in an aspirin challenge at baseline and the end of the 3-week treatment. Four tablets, each containing 325 mg of aspirin, are given 12 h before ingestion of the sugar mixture and another four tablets 1 h before taking the sugar drink. Measurement of urinary sugars using GC is identical to that of the sugar test without aspirin challenge.

Example 34

Plasma and Serum Measures of Endotoxin Exposure

Increased intestinal permeability strongly correlates with markers of increased exposure to endotoxin, a marker indicating increased oxidative stress burden in the intestine. To determine if the increased permeability observed in the study is associated with increased translocation of intestinal bacterial product, serum endotoxin and LPS-binding protein is measured after aspirin challenge. In addition to the more commonly-measured endotoxin, LPS-binding protein is another index of intestinal permeability-related systemic exposure to intestinal bacterial products. Endotoxin is measured in serum by Limulus Amebocyte Lysate QCL-1000 (Lonza #50-647U). Serum samples are diluted at a 1:5 ratio with LAL reagent water. Lipopolysaccharide binding protein (LBP) is measured in plasma using an ELISA kit from Cell Sciences Inc (# HK315).

Example 35

Serum Complete Metabolic Panel

A Complete Metabolic Panel is performed to assess the effect the treatments on each patient's basic physiology. Measurements include sodium, potassium, chloride, $CO_2$, blood urea nitrogen, creatinine, glucose, total protein, albumin, calcium, total bilirubin, alkaline phosphatase, aspartate aminotransferase, alanine aminotransferase, and anion gap.

Example 36

Test for Associations

Associations between host metabolic and immunological markers, all taxa in the gut microbiota (analyzed at different taxonomic levels) and *Bifidobacterium* populations are assessed by multiple-correlation analysis using Pearson's correlation tests using GraphPad Prism software. Data that does not conform to normal distribution and cannot be normalized with mathematical transformations (i.e.: log 10, square root) is analyzed with Spearmen's rank correlations.

Example 37

Outcomes

The probiotic, GOS, or the synbiotic significantly contributes to metabolic improvements when compared to the control placebo. Decreased intestinal hyperpermeability occurs in the InVivoSyn synbiotic group over that of the commercially available synbiotic as well as the probiotics and prebiotics alone. A decrease in endotoxemia and an increase in LPS-binding protein is observed, as lower levels of plasma LBP have been associated with increased exposure to gram negative bacteria.

Either the probiotic, GOS, or the synbiotic significantly contributes to metabolic improvements when compared to the control placebo (lactose), and a correlation between the *Bifidobacterium* population and metabolic markers is detectable.

Example 38

Statistical Analysis

Statistical tests for treatment effects on the abundance of individual taxonomic ranks is performed by one-way analysis of variance (ANOVA) with repeated measures followed by Tukey's post hoc multiple comparisons tests. Apart from understanding how each individual taxa is affected by the treatments, a collective understanding of how these groups of data are affected is investigated by multivariate analyses such as Principal Components Analysis (PCA). For the microbial data, PCAs are constructed from a phylogenetic perspective using UniFrac software. In addition, one-way ANOVA tests followed by Tukey's post hoc tests are performed to identify differences in population size and/or metabolic activity in the different treatment groups, and especially between synbiotic and probiotic groups. Data is presented as mean±SEM for variables that can be considered normally distributed (or median and range for variables not normally distributed). Group means is compared by ANOVA and post-hoc tests except when data is not normally distributed, in which case nonparametric analyses of medians is done using the Kruskal-Wallis test. Correlation analysis is done using the Pearson correlation test for parametric analysis and the Spearman correlation test for nonparametric analysis. Chi-square tests or Fisher's Exact Tests is used for incidence data. $p<0.05$ defines statistical significance. All analyses use SPSS (Chicago, Ill.) or SAS. Data that does not conform to normal distribution and cannot be normalized with mathematical transformations (i.e., log 10, square root) is analyzed with Freidman's non-parametric tests.

Sequence of 16S rDNA from microbial strain BD1 (SEQ ID NO:8)

```
TGCAGTCGAA CGGGATCCCA GGAGCTTGCT CCTGGGTGAG AGTGGCGAAC GGGTGAGTAA

TGCGTGACCG ACCTGCCCCA TACACCGGAA TAGCTCCTGG AAACGGGTGG TAATGCCGGA

TGCTCCAGTT GACCGCATGG TCCTCTGGGA AAGCTTTTGC GGTATGGGAT GGGGTCGCGT

CCTATCAGCT TGATGGCGGG GTAACGGCCC ACCATGGCTT CGACGGGTAG CCGGCCTGAG

AGGGCGACCG GCCACATTGG GACTGAGATA CGGCCCAGAC TCCTACGGGA GGCAGCAGTG

GGGAATATTG CACAATGGGC GCAAGCCTGA TGCAGCGACG CCGCGTGCGG GATGACGGCC

TTCGGGTTGT AAACCGCTCT TGACTGGGAG CAAGCCCTTC GGGGTGAGTG TACCTTTCGA

ATAAGCACCG GCTAACTACG TGCCAGCAGC CGCGGTAATA CGTAGGGTGC AAGCGTTATC

CGGAATTATT GGGCGTAAAG GGCTCGTAGG CGGTTCGTCG CGTCCGGTGT GAAAGTCCAT

CGCTTAACGG TGGATCCGCG CCGGGTACGG GCGGGCTTGA GTGCGGTAGG GGAGACTGGA

ATTCCCGGTG TAACGGTGGA ATGTGTAGAT ATCGGGAAGA ACACCAATGG CGAaGGCAGG

TCTCTGGGCC GTCACTGACG CTGAGGAGCG AAAGCGTGGG GAGCGAACAG GATTAGATAC

CCTGGTAGTC CACGCCGTAA ACGGTGGATG CTGGATGTGG GGACCATTCC ACGGTCTCCG

TGTCGGAGCC AACGCGTTAA GCATCCCGCC TGGGGAGTAC GGCCGCAAGG CTAAAACTCA

AAGAAATTGA CGGGGGCCCG CACAAGCGGC GGAGCATGCG GATTAATTCG ATGCAACGCG

AAGAACCTTA CCTGGGCTTG ACATGTTCCC GACAGCCGTA GAGATACGGT CTCCCTTCGG

GGCGGGTTCA CAGGTGGTGC ATGGTCGTCG TCAGCTCGTG TCGTGAGATG TTGGGTTAAG

TCCCGCAACG AGCGCAACCC TCGCCCTGTG TTGCCAGCAC GTCGTGGTGG GAACTCACGG

GGGACCGCCG GGGTCAACTC GGAGGAAGGT GGGGATGACG TCAGATCATC ATGCCCCTTA

CGTCCAGGGC TTCACGCATG CTACAATGGC CGGTACAACG GGATGCGACA CTGTGAGGTG

GAGCGGATCC CTTAAAACCG GTCTCAGTTC GGATTGGAGT CTGCAACCCG ACTCCATGAA

GGCGGAGTCG CTAGTAATCG CGGATCAG
```

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A foodstuff comprising (a) a composition comprising *Bifidobacterium adolescentis* strain BD1 and GOS and a pharmaceutically acceptable carrier selected from the group consisting of a liquid carrier, a gel-based carrier, an oleaginous carrier, and an emulsion; and (b) yogurt.

2. A method for establishing or maintaining a healthy gastrointestinal flora in an animal, said method comprising administering, enterally, an effective amount of the foodstuff of claim 1 to the animal,
   thereby establishing or maintaining a healthy gastrointestinal flora in the animal.

3. The method of claim 2, wherein said animal is a human.

4. The method of claim 2, wherein said effective amount is from about $10^2$ CFU/day to about $10^{12}$ CFU/day.

5. A method for reducing the effects of a gastrointestinal disease in an animal, said method comprising administering, enterally, an effective amount of the foodstuff of claim 1 to the animal,
   thereby reducing the effects of a gastrointestinal disease in the animal.

6. The method of claim 5, wherein said animal is a human.

7. The method of claim 5, wherein said effective amount is from about $10^2$ CFU/day to about $10^{12}$ CFU/day.

\* \* \* \* \*

```
                              SEQUENCE LISTING

<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide

<400> SEQUENCE: 1
tcgcgtcygg tgtgaaag                                                      18

<210> SEQ ID NO 2
<211> LENGTH: 17
<212> TYPE: DNA
<213> ORGANISM: Artificial Sequence
<220> FEATURE:
<223> OTHER INFORMATION: Oligonucleotide

<400> SEQUENCE: 2
ccacatccag crtccac                                                       17

<210> SEQ ID NO 3
<211> LENGTH: 60
<212> TYPE: DNA
<213> ORGANISM: Artificial Sequence
<220> FEATURE:
<223> OTHER INFORMATION: Oligonucleotide

<400> SEQUENCE: 3
cgcccgccgc gcgcggcggg cggggcgggg gcacgggggg actcctacgg gaggcagcag        60

<210> SEQ ID NO 4
<211> LENGTH: 14
<212> TYPE: DNA
<213> ORGANISM: Artificial Sequence
<220> FEATURE:
<223> OTHER INFORMATION: Oligonucleotide

<400> SEQUENCE: 4
accgcggctg ctgg                                                          14

<210> SEQ ID NO 5
<211> LENGTH: 50
<212> TYPE: DNA
<213> ORGANISM: Artificial Sequence
<220> FEATURE:
<223> OTHER INFORMATION: Oligonucleotide

<400> SEQUENCE: 5
cctatcccct gtgtgccttg gcagtctcag agagtttgat cmtggctcag                   50
```

```
<210> SEQ ID NO 6
<211> LENGTH: 50
<212> TYPE: DNA
<213> ORGANISM: Artificial Sequence
<220> FEATURE:
<223> OTHER INFORMATION: Oligonucleotide

<400> SEQUENCE: 6
cctatcccct gtgtgccttg gcagtctcag agggttcgat tctggctcag          50

<210> SEQ ID NO 7
<211> LENGTH: 55
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 31, 32, 33, 34, 35, 36, 37, 38
<223> OTHER INFORMATION: n = any nucleotide

<400> SEQUENCE: 7
ccatctcatc cctgcgtgtc tccgactcag nnnnnnnnat taccgcggct gctgg     55

<210> SEQ ID NO 8
<211> LENGTH: 1288
<212> TYPE: DNA
<213> ORGANISM: Bifidobacterium adolescentis

<400> SEQUENCE: 8
tgcagtcgaa cgggatccca ggagcttgct cctgggtgag agtggcgaac gggtgagtaa    60
tgcgtgaccg acctgcccca tacaccggaa tagctcctgg aaacgggtgg taatgccgga   120
tgctccagtt gaccgcatgg tcctctggga aagcttttgc ggtatgggat ggggtcgcgt   180
cctatcagct tgatggcggg gtaacggccc accatggctt cgacgggtag ccggcctgag   240
agggcgaccg gccacattgg gactgagata cggcccagac tcctacggga ggcagcagtg   300
gggaatattg cacaatgggc gcaagcctga tgcagcgacg ccgcgtgcgg gatgacggcc   360
ttcgggttgt aaaccgctct tgactgggag caagcccttc ggggtgagtg tacctttcga   420
ataagcaccg gctaactacg tgccagcagc cgcggtaata cgtagggtgc aagcgttatc   480
cggaattatt gggcgtaaag ggctcgtagg cggttcgtcg cgtccggtgt gaaagtccat   540
cgcttaacgg tggatccgcg ccgggtacgg gcgggcttga gtgcgtagg ggagactgga   600 attcccggtg taacggtgga atgtgtagat atcgggaaga acaccaatgg cgaaggcagg   660
tctctgggcc gtcactgacg ctgaggagcg aaagcgtggg gagcgaacag gattagatac   720
cctggtagtc cacgccgtaa acggtggatg ctggatgtgg ggaccattcc acggtctccg   780
tgtcggagcc aacgcgttaa gcatcccgcc tggggagtac ggccgcaagg ctaaaactca   840
aagaaattga cgggggcccg cacaagcggc ggagcatgcg gattaattcg atgcaacgcg   900
aagaacctta cctgggcttg acatgttccc gacagccgta gagatacggt ctcccttcgg   960
ggcgggttca caggtggtgc atggtcgtcg tcagctcgtg tcgtgagatg ttgggttaag  1020
tcccgcaacg agcgcaaccc tcgccctgtg ttgccagcac gtcgtggtgg gaactcacgg  1080
gggaccgccg gggtcaactc ggaggaaggt ggggatgacg tcagatcatc atgcccctta  1140
cgtccagggc ttcacgcatg ctacaatggc cggtacaacg ggatgcgaca ctgtgaggtg  1200
gagcggatcc cttaaaaccg gtctcagttc ggattggagt ctgcaacccg actccatgaa  1260
ggcggagtcg ctagtaatcg cggatcag                                    1288
```